(12) United States Patent
Saw et al.

(10) Patent No.: US 9,486,228 B2
(45) Date of Patent: Nov. 8, 2016

(54) OSTEOTOMY BELOW THE TIBIAL TUBEROSITY BY MULTIPLE DRILLING

(71) Applicant: KLSMC STEM CELLS SDN BHD, Kuala Lumpur (MY)

(72) Inventors: Khay Yong Saw, Kuala Lumpur (MY); Reza Ching Soong Ng, Kuala Lumpur (MY); Caroline Siew Yoke Jee, Kuala Lumpur (MY)

(73) Assignee: KLSMC STEM CELLS SDN BHD, Kuala Lumpur (MY)

( * ) Notice: Subject to any disclaimer, the term of this patent is extended or adjusted under 35 U.S.C. 154(b) by 137 days.

(21) Appl. No.: 14/047,236

(22) Filed: Oct. 7, 2013

(65) Prior Publication Data
US 2015/0071885 A1 Mar. 12, 2015

(30) Foreign Application Priority Data
Sep. 12, 2013 (MY) .............................. 20130701639

(51) Int. Cl.
*A61B 17/15* (2006.01)
*A61B 17/17* (2006.01)
*A61K 35/14* (2015.01)
*A61B 17/80* (2006.01)

(52) U.S. Cl.
CPC ......... *A61B 17/1764* (2013.01); *A61B 17/151* (2013.01); *A61B 17/152* (2013.01); *A61B 17/157* (2013.01); *A61B 17/8095* (2013.01); *A61K 35/14* (2013.01)

(58) Field of Classification Search
CPC ........................... A61B 17/152; A61B 17/157
USPC .......................................................... 606/88
See application file for complete search history.

(56) References Cited

U.S. PATENT DOCUMENTS

| 5,575,982 A | 11/1996 | Reiss et al. | |
|---|---|---|---|
| 5,601,565 A * | 2/1997 | Huebner ............... | A61B 17/15 606/79 |
| 5,613,969 A * | 3/1997 | Jenkins, Jr. ........... | A61B 17/15 606/87 |

(Continued)

FOREIGN PATENT DOCUMENTS

| WO | 96/24295 | 8/1996 |
|---|---|---|
| WO | 96/242295 | 8/1996 |

OTHER PUBLICATIONS

Berz et al., "Cryopreservation of hematopoietic stem cells," American Journal of Hematology, vol. 82, No. 6, Jun. 2007, pp. 463-472.

(Continued)

*Primary Examiner* — David Bates
(74) *Attorney, Agent, or Firm* — Hamre, Schumann, Mueller & Larson, P.C.

(57) ABSTRACT

Surgical devices, kits and methods of using thereof are described. Generally, the surgical kit includes an osteotomy guide device and/or a bone spacer guide device. The surgical kit can be used in a surgical method for correcting a malalignment of the knee joint that involves performing a fibular osteotomy and/or a tibial osteotomy, and/or administering stem cells. Generally, the osteotomy guide device is configured to allow drilling to occur around the tibia and across a horizontal cross-sectional plane of the tibia so that a direction of each of the drill holes that are formed in the tibia is substantially parallel to or on the same horizontal cross-sectional plane of the tibia. The osteotomy guide device allows drilling to be conducted efficiently and accurately.

12 Claims, 18 Drawing Sheets

(56) References Cited

U.S. PATENT DOCUMENTS

| | | | |
|---|---|---|---|
| 5,722,978 A * | 3/1998 | Jenkins, Jr. | A61B 17/152 606/79 |
| 5,749,875 A | 5/1998 | Puddu | |
| 5,980,526 A * | 11/1999 | Johnson | A61B 17/152 606/86 R |
| 6,190,390 B1 * | 2/2001 | McAllister | A61B 17/1604 606/54 |
| 6,203,546 B1 | 3/2001 | MacMahon | |
| 6,796,986 B2 | 9/2004 | Duffner | |
| 8,236,000 B2 | 8/2012 | Ammann et al. | |
| 8,241,292 B2 * | 8/2012 | Collazo | A61B 17/152 606/86 R |
| 8,617,166 B2 * | 12/2013 | Hanson | A61B 17/1764 606/86 R |
| 2003/0171757 A1 * | 9/2003 | Coon | A61B 17/157 606/87 |
| 2005/0075641 A1 * | 4/2005 | Singhatat | A61B 17/15 606/86 R |
| 2006/0106396 A1 * | 5/2006 | Justin | A61B 17/15 606/87 |
| 2006/0122617 A1 * | 6/2006 | Lavallee | A61B 17/155 606/87 |
| 2006/0241636 A1 * | 10/2006 | Novak | A61B 17/15 606/87 |
| 2008/0039857 A1 * | 2/2008 | Giersch | A61B 17/1703 606/96 |
| 2008/0077151 A1 * | 3/2008 | Kring | A61B 17/132 606/88 |
| 2008/0114366 A1 * | 5/2008 | Smucker | A61B 17/158 606/88 |
| 2008/0177306 A1 | 7/2008 | Lamborne et al. | |
| 2008/0195099 A1 | 8/2008 | Minas | |
| 2008/0262500 A1 * | 10/2008 | Collazo | A61B 17/152 606/88 |
| 2009/0157190 A1 | 6/2009 | Collazo et al. | |
| 2010/0274254 A1 * | 10/2010 | Boileau | A61B 17/1725 606/93 |
| 2011/0218542 A1 * | 9/2011 | Lian | A61B 17/56 606/88 |
| 2011/2013376 | 9/2011 | Maxson et al. | |
| 2013/0079784 A1 * | 3/2013 | Vail | A61B 17/158 606/88 |
| 2015/0196308 A1 * | 7/2015 | Wilkinson | A61B 17/155 606/88 |
| 2016/0100845 A1 * | 4/2016 | Smith | A61B 17/74 606/89 |

OTHER PUBLICATIONS

European Search Report from corresponding European patent application 13185055.4-1506, dated Mar. 21, 2014 (11 pages total).

Partial European Search Report from corresponding European patent application, dated Jan. 8, 2014 (5 pages total).

Marmotti et al., "Bone marrow-derived cell mobilization by G-CSF to enhance osseointegration of bone substitute in high tibial osteotomy," Knee Surg Sports Traumatol Arthrosc, 2013; 21(1) 237-248.

Shim et al., "High tibial open wedge osteotomy below the tibial tubercle: clinical and radiographic results," Knee Surg Sports Traumatol Arthrosc. 2013; 21(1): 57-63.

Wakitani et al., "Human autologous culture expanded bone marrow mesenchymal cell transplantation for repair of cartilage defects in osteoarthritic knees," Journal of the OsteoArthritis Research Society International. 2002; 10:199-206.

Dallari et al., "Enhanced tibial osteotomy healing with use of bone grafts supplemented with platelet gel or platelet gel and bone marrow stromal cells," J Bone Joint Surg Am. 2007; 89(11):2413-2420.

Flierl et al., "Open wedge high tibial osteotomy using fractioned drill osteotomy using fractioned drill osteotomy: a surgical modification that lowers the complication rate," Knee Surg Sports Traumatol Arthrosc. 1996; 4(3): 149-153.

* cited by examiner

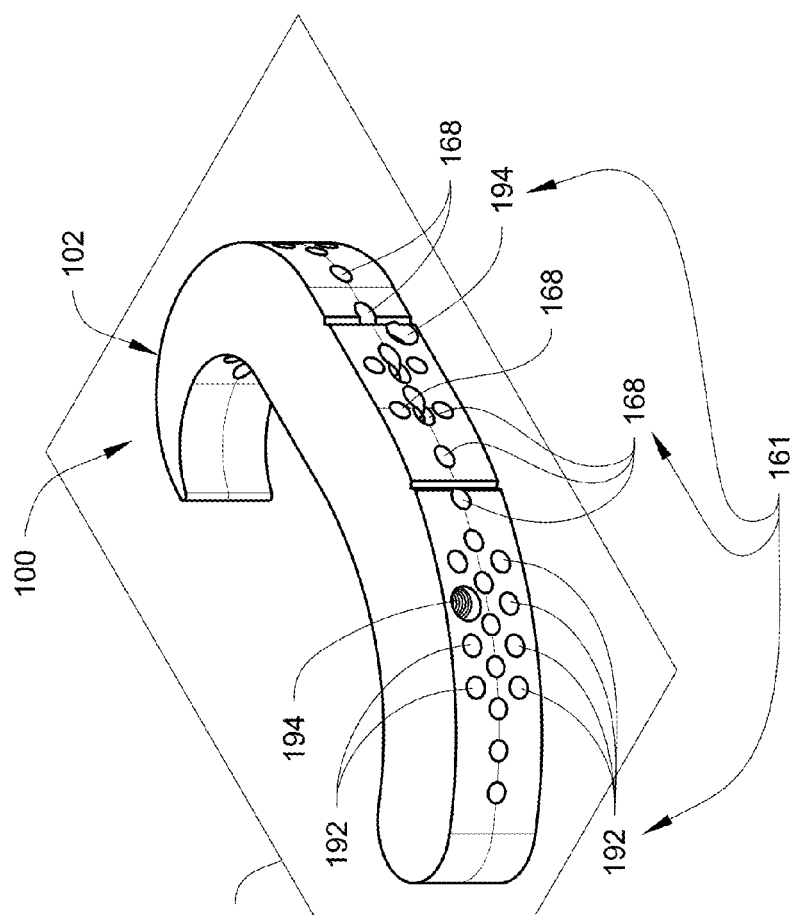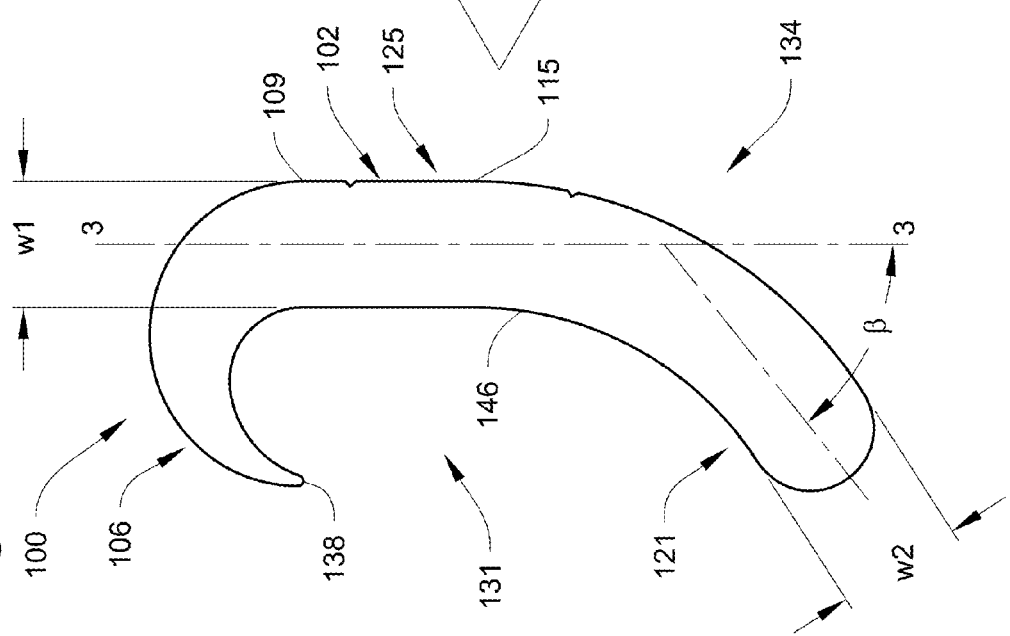

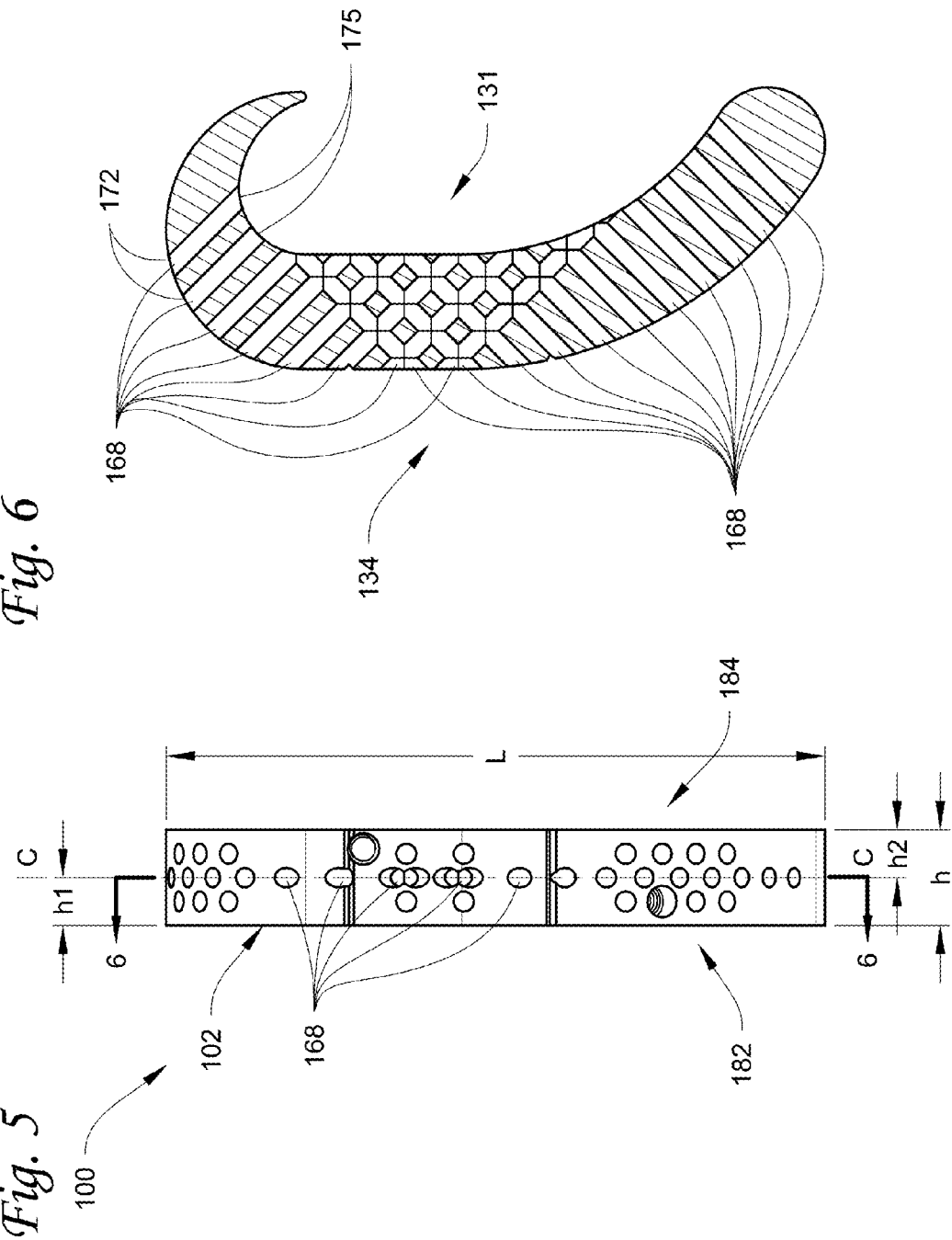
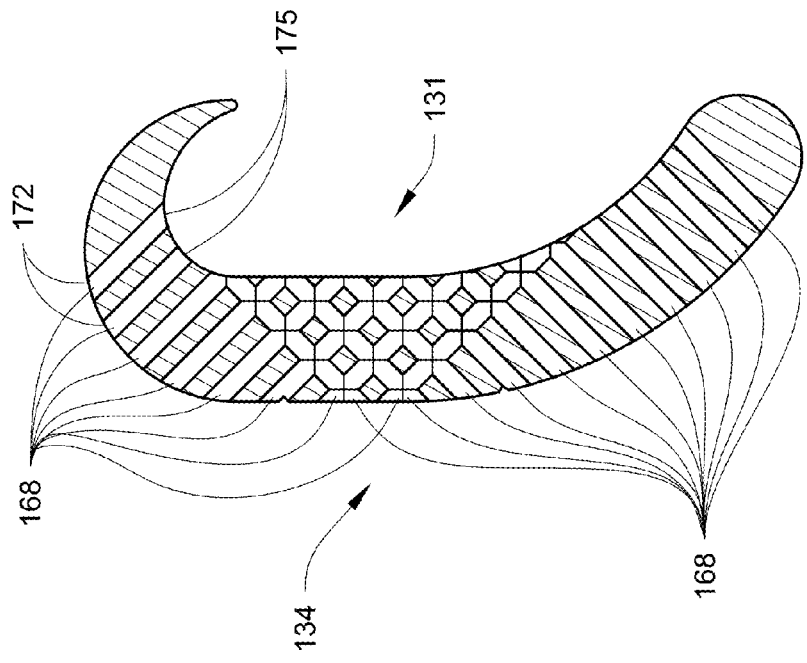

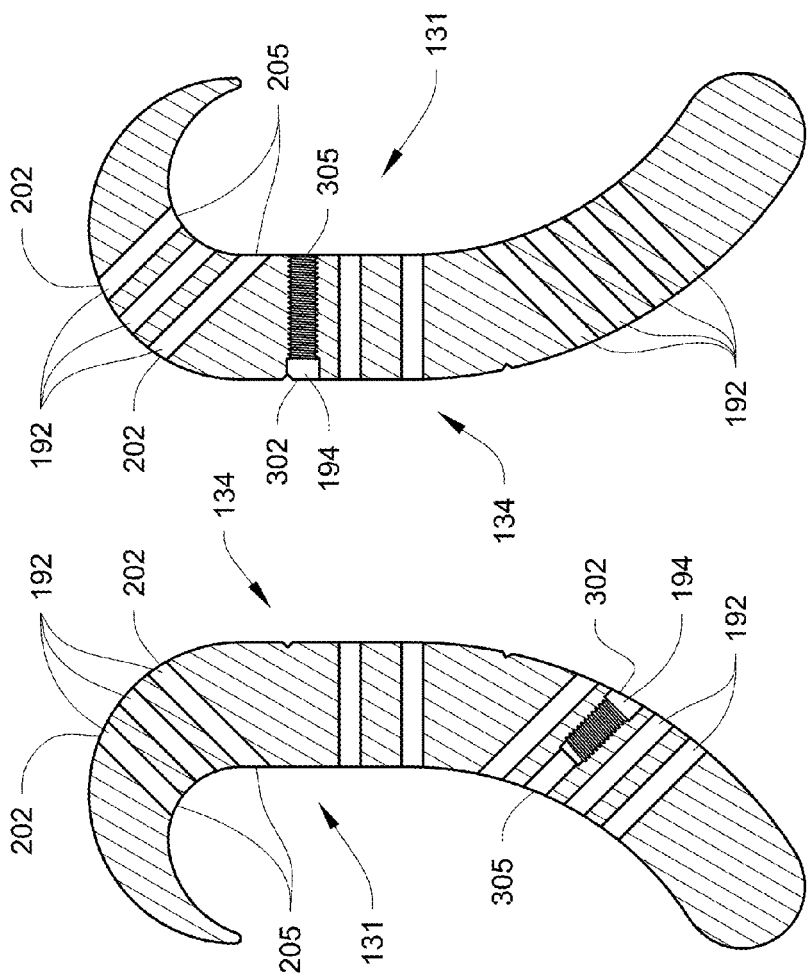

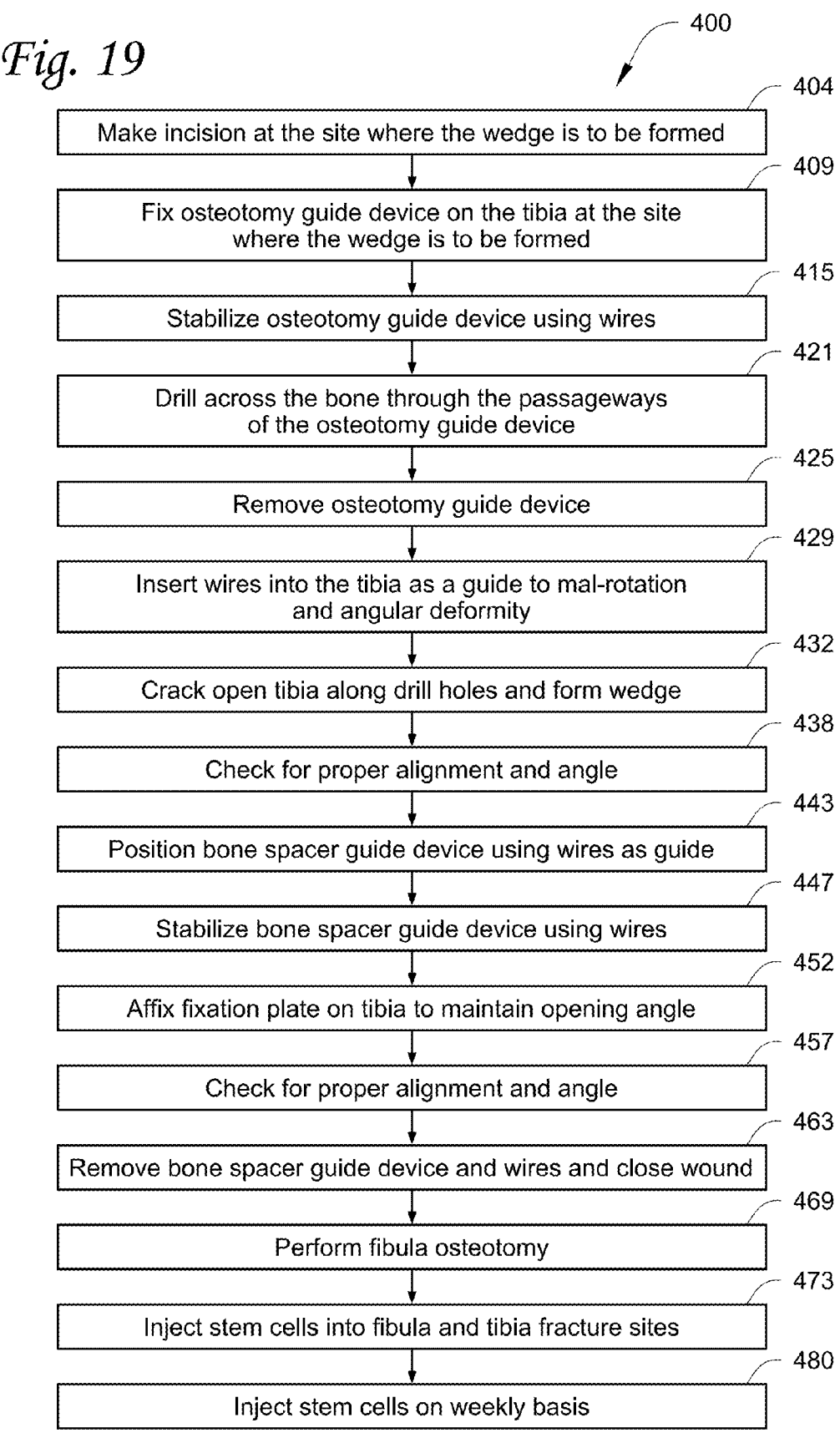

Fig. 19

- Make incision at the site where the wedge is to be formed
- Fix osteotomy guide device on the tibia at the site where the wedge is to be formed
- Stabilize osteotomy guide device using wires
- Drill across the bone through the passageways of the osteotomy guide device
- Remove osteotomy guide device
- Insert wires into the tibia as a guide to mal-rotation and angular deformity
- Crack open tibia along drill holes and form wedge
- Check for proper alignment and angle
- Position bone spacer guide device using wires as guide
- Stabilize bone spacer guide device using wires
- Affix fixation plate on tibia to maintain opening angle
- Check for proper alignment and angle
- Remove bone spacer guide device and wires and close wound
- Perform fibula osteotomy
- Inject stem cells into fibula and tibia fracture sites
- Inject stem cells on weekly basis

OSTEOTOMY BELOW THE TIBIAL TUBEROSITY BY MULTIPLE DRILLING

FIELD OF THE INVENTION

The embodiments disclosed herein relate generally to surgical devices, kits and methods that involve the use thereof. In particular, the methods of using the surgical devices and kits can involve performing tibial and/or fibular osteotomies and/or administering stem cells.

BACKGROUND OF THE INVENTION

Varus or valgus deformity, which is a malalignment or misalignment of the knee, can be caused by several factors including for example wear and tear of the cartilage, misalignment at birth, post-traumatic fracture, osteoarthritis or rheumatoid arthritis. Current available treatments are limited to tibial osteotomy (open or closed, with or without bone graft) or unicondylar knee replacementor a total knee replacement. The degree of deformities and the patient age are usually the two main factors that decide which is the better option. The former method has been performed on younger patients while the latter on patients over 50 years.

Currently performed osteotomy methods can correct misalignment, but in general, these methods involve the use of complicated tools and in many cases, can lead to non-union. Knee replacements also can lead to complications, for example, infection, blood clots and injury to nerves or vessels. In addition, knee replacements generally involve replacement of a natural part of the body with a synthetic component, which needs to be replaced via another surgery when the synthetic component reaches its lifespan. Moreover, this procedure is generally not recommended for younger and/or active patients as the prosthesis cannot offer a high functional activity level and does not last throughout the lifetime of the patient.

Currently, osteotomy is generally performed above the tibial tuberosity at the level of the cancellous bone, which can cause tibial plateau fracture or collapse.

SUMMARY OF THE INVENTION

The aspects and embodiments described herein are directed to surgical devices, kits and methods of using the surgical kit. Generally, the surgical kit includes an osteotomy guide device and/or a bone spacer guide device. The surgical kit can be used in a surgical method for correcting a misalignment of a lower limb, e.g., a knee joint, that involves a fibular osteotomy, a tibial osteotomy, and/or administration of stem cells. In some examples, the surgical method involves correction of a varus deformity.

In general, the disclosed method involves performing tibial osteotomy below the tibial tuberosity. Generally, affixation of a fixing plate is better when performing tibial osteotomy below the tibial tuberosity, as compared to when performing tibial osteotomy above the tibial tuberosity because there is less chance of the cancellous bone collapsing. However, tibial osteotomy below the tibial tuberosity involves cutting into the cortical bone, whereas tibial osteotomy above the tibial tuberosity involves cutting into the cancellous bone. It is generally accepted that healing rates of the cortical bone are slower than those of the cancellous bone such that there is a high probability that tibial osteotomy below the tibial tuberosity may lead to non-union following the procedure, for example, for older patients who are in the fourth decade or more of their lives, thereby rendering the procedure a failure. Thus, tibial osteotomy below the tibial tuberosity is generally not recommended to relatively older patients, for example, older patients who are in the fourth decade or more of their lives.

The present inventors have found that the disclosed method that involves, e.g., the use of the disclosed surgical kit in performing fibular osteotomy and/or tibial osteotomy, for example, performed below the tibial tuberosity, can lead to successful union of the bone following the procedure(s), even in relatively older patients, such as for example, patients who are past the fourth decade of their lives. Note that a fibular osteotomy can be generally performed when a tibial osteotomy is performed below the tibial tuberosity. The disclosed methods also can lead to: (1) correction of misalignment; (2) regeneration of the bone in a relatively short time period as compared to that of conventional methods; (3) minimizing neurovascular bundle injury; (4) reducing stiffness in the knee after the procedure; (5) a smaller incision at the site of the respective osteotomies as compared to that of conventional methods; (6) ease in performing the surgery; and (7) minimum disruption of the periosteum as compared to that of conventional methods which involve sawing.

In one embodiment, the surgical kit is used for performing fibular and/or tibial osteotomy. In some examples, the tibial osteotomy can involve drilling of the tibia at a tibial osteotomy site through the cortices of the bone. In some examples, drilling of the tibia can involve the use of a drill and a cutting tool as generally known in the art. In some examples, the cutting tool utilized can be a drill bit to create drill holes in the tibia.

In some examples, the fibular osteotomy can be performed at a fibular osteotomy site, for example, at a distal third position of the fibula as is generally known in the art. In some examples, the fibular osteotomy can be conducted at approximately 45±15 degrees relative to a neutral axis 1-1.

In one embodiment, the surgical kit includes an osteotomy guide device. Generally, the osteotomy guide device is configured to allow drilling to occur around the tibia and across a horizontal cross-sectional plane of the tibia so that the direction of each of the drill holes that are formed in the tibia is substantially parallel to or on the same horizontal cross-sectional plane of the tibia. The osteotomy guide device allows drilling to be conducted efficiently and accurately.

In one embodiment, the osteotomy guide device has a base having a central portion, an upwardly extending portion and a downwardly extending portion. In some examples, the central portion is an elongated portion that extends from a first end to a second end, thereby defining a vertical axis when the device is viewed in top view. In some examples, the upwardly extending portion extends upwardly from the first end of the central portion while the downwardly extending portion extends downwardly from the second end of the central portion.

In some examples, of such an embodiment the upwardly extending portion is a latching portion. In some examples, the latching portion is in the shape of a hook and is dimensioned so that a tip of the hook can latch onto a tibia. In some examples, the latching portion hooks toward an inner side of the base. In some examples, the latching portion functions to fix the device onto the tibia so that the device is in a fixed state.

In some examples, the downwardly extending portion includes a flared portion that has a curvature. In some examples, the flared portion curves toward the inner side of the base. In some examples, the angle of the curvature can be about 0 to about 90 degrees relative to the vertical axis defined by the central portion. In some examples, the angle of the curvature can be 0±15 to 90±15 degrees relative to the vertical axis defined by the central portion. In some examples, the angle of the curvature can be 45±15 degrees.

In some examples the angle of curvature of the flared portion can be about 0 to 45 degrees relative to the vertical axis defined by the central portion, more particularly 30 to 45 degrees, 35 to 45 degrees, or 40 to 45 degrees relative to the vertical axis defined by the central portion.

In some examples, the osteotomy guide comprises a central portion, an upwardly extending portion and a downwardly extending portion, wherein the central portion is an elongated portion that defines a vertical axis, the elongated portion having an inner side and an opposite outward side wherein in use, when the device positioned in the body, the inner side is located against the bone (tibia), and the outward side is accessible. In such examples the upwardly extending portion can form a curved hook wherein the inner side of the elongated portion forms the inside of the hook, and the downwardly extending portion includes a flared portion that has a curvature such that as the downwardly extending portion extends it curves such that the inner side of the elongated portion is the inner surface of the curve of the flared portion and the outward side of the elongated portion is the outside surface of the curve of the flared portion.

In some examples, the length of the osteotomy guide device along the vertical axis can be about 60 to 80 mm, more particularly 65 to 75 mm, more particularly about 68 to 70 mm. In some examples, the tip of the curved hook of the upwardly extending portion and the tip of the flared portion of the downwardly extending portion are in a vertical axis spaced apart from the inner side of the central portion by about 16 to 18 mm. In some examples, the central portion and the flared portion are generally continuous so that an outline of the central portion and the flared portion generally follows, at least in part, an outline of a cross-section of the tibia when the device is in the fixed state.

In other examples, the central portion and flared portion can be manufactured in a plurality of parts wherein the parts can be conjoined together to form the complete device. In some examples, the plurality of parts when conjoined together can be provided with a locking mechanism to retain the parts in the form of the complete device. In some examples, the base of the osteotomy guide device includes a plurality of passageways that are formed through a thickness of the base. In some examples, some of the passageways are adapted for positioning a direction of the drilling. In some examples, some of the passageways are adapted for inserting a handle or a stabilizing member, e.g., a wire. In some examples, the base has a median axis, a first sagittal axis and a second sagittal axis as viewed in side view. The median axis is substantially parallel to a median plane of the base, where the median plane is a plane that divides the device into substantially two equal halves. The first and second sagittal axes are substantially parallel to the median axis.

In some examples the device can be formed of stainless steel or titanium or titanium alloys.

In some examples, each of the passageways that are adapted for positioning the direction of the drill has an inlet and an outlet, and the inlets and/or outlets are provided along the median axis of the base. In some examples, each of the passageways extends from the inlet to the outlet in a direction that is substantially parallel to or on a horizontal cross-sectional plane when the device is in the fixed state. In some examples two passageways are provided in the central portion in a first sagittal axis and two passageways in a second sagittal axis. In some examples the passageways can be spaced apart along a vertical axis by 6 mm (spacing from a central point of one of the passageways to the other, not from one edge of the passageway to another). In some examples 15 to 20 passageways, suitably 19 passageways are provided in the device. In some examples, passageways are provided in the upwardly extending portion in a first sagittal axis, median axis and second sagittal axis. In some examples, passageways are provided in the downwardly extending portion in a first sagittal axis, median axis and second sagittal axis. In some examples, about 9 passageways can be provided in the upwardly extending portion and about 10 passageways can be provided in the downwardly extending portion. In some examples the passageways can be spaced apart by 4 mm. In some examples the passageways along the median axis are offset from those of the first and second sagittal axis. In some examples, at least one of the passageways, suitably two of the passageways provided are adapted to receive a handle such that a user can hold the device by the handle rather than gripping the actual device when it is inserted into the surgical site. In some examples, such a passageway may be adapted to allow a portion of the handle to screw into the passageway such that the device can be held by the handle.

In some examples, each of the passageways that are adapted for positioning a stabilizing member, e.g., a wire, and/or a handle has an inlet and an outlet. In some examples, the inlets and/or outlets are formed along the first sagittal axis and/or the second sagittal axis.

In one embodiment, the surgical kit further includes a bone spacer guide device. In some examples, the device has a main body having a central portion with two opposing side portions that extend outwardly from the central portion. The central portion has a downwardly extending wedge portion. In some examples, the wedge portion may be detached from the main body. In some examples, each of the side portions includes a groove adjacent the central portion, and an arm portion that extends from the groove. In some examples, the grooves are adapted for positioning a stabilizing member, e.g., wires such as k-wires. In some examples, each of the arm portions include passageways adapted for inserting a stabilizing member, e.g., a wire such as a k-wire, for example, in parallel to one another and/or perpendicular to the long-axis of the tibia so as to stabilize the device.

In one embodiment, the disclosed method involves the use of the surgical kit. In some examples, fibular osteotomy and/or tibial osteotomy is performed. In some examples, the tibial osteotomy is performed below the tibial tuberosity. In some instances, the tibial osteotomy is performed at a distal insertion of a patella tendon below the tibial tuberosity.

In some examples, the method involves fixing the osteotomy guide device on a tibia, stabilizing the osteotomy guide device, for example, a stabilizing member such as a wire, pin or screw, drilling across the bone through the passageways of the osteotomy guide device, removing the osteotomy guide device, cracking open the tibia along the drill holes that are formed in the tibia to form an opening in the tibia, inserting an osteotome into the opening to produce a wedge with a desired wedge angle, providing the bone spacer guide device on the tibia so that the wedge is maintained at a desired angle, affixing a fixation plate on the tibia, removing the bone spacer guide device and any stabilizing members, closing the wound, and/or injecting stem cells into the fibular osteotomy fracture site and/or the tibial osteotomy fracture site.

Accordingly, a first aspect of the invention provides a surgical kit comprising an osteotomy guide device as disclosed herein and/or a bone spacer guide device as disclosed herein.

According to a second aspect of the present invention there is provided the use of the surgical kit of the first aspect of the present invention in performing fibular and/or tibial osteotomy.

According to a third aspect of the present invention there is a provided a method of performing fibular and/or tibial osteotomy comprising providing a surgical kit of the first aspect of the present invention to a subject in need thereof.

In one embodiment, the method of performing a tibial osteotomy can involve drilling of the tibia at a tibial osteotomy site through the cortices of the bone. In one embodiment, drilling of the tibia can involve the use of a drill and a cutting tool as generally known in the art. In one embodiment, the cutting tool utilized can be a drill bit to create drill holes in the tibia.

In one embodiment, the fibular osteotomy can be performed at a fibular osteotomy site, for example, at a distal third position of the fibula as is generally known in the art. In some examples, the fibular osteotomy can be conducted at approximately 45±15 degrees relative to a neutral axis 1-1.

According to a fourth aspect of the present invention there is provides the use of stem cells to repair a fibular or tibial osteotomy fracture site and to encourage the successful union of bone at the fracture site. In one embodiment, the stem cells are peripheral blood stem cells. In one embodiment, the peripheral blood stem cells are administered in an effective amount for repairing the tibial or fibular osteotomy fracture site. In one embodiment, the effective amount of peripheral blood stem cells is from about $0.2 \pm 0.1 \times 10^{6 \pm 1}$ to about $8 \pm 1 \times 10^{6 \pm 2}$. In one embodiment, the stem cells are administered about one per week for about 1 to 5 weeks. In one embodiment the stem cells are provided to the subject following the method of the third aspect of the invention. In one embodiment stem cells or means to deliver stem cells are provided as part of the surgical kit of the first aspect of the invention.

According to a fifth aspect of the invention there is provided a process to provide stem cells for use in a method of the present invention, wherein the process comprises the steps:
  providing harvested stem cells,
  preparing a mixture of the harvested stem cells and saline, plasma and dimethydisulphoxide (DMSO)
  freezing the mixture to about −80° C. for approximately at least 45 minutes, and
  freezing the mixture to about −196° C.

In one embodiment the harvested stem cells are peripheral blood stem cells (PBSCs). In some examples, the PBSCs are positive for CD34. In some examples the saline of the mixture can be cooled to about 4° C.

Other aspects of the invention will become apparent by consideration of the detailed description and accompanying drawings.

BRIEF DESCRIPTION OF THE DRAWINGS

FIG. 3 illustrates a top plan view of the osteotomy guide device shown in FIG. 2.

FIG. 4 illustrates a schematic view of the osteotomy guide device shown in FIG. 2.

FIG. 5 illustrates a side view of the osteotomy guide device shown in FIG. 2 showing a median axis C-C.

FIG. 6 illustrates a cross-sectional top view of the osteotomy guide device shown in FIG. 2 taken across the median axis C-C shown in FIG. 5.

FIG. 7 illustrates a side view of the osteotomy guide device shown in FIG. 2 showing first and second sagittal axes A-A and B-B.

FIG. 8 illustrates a cross-sectional top view of the osteotomy guide device shown in FIG. 2 taken across the first sagittal axis A-A shown in FIG. 7.

FIG. 9 illustrates a cross-sectional side view of the osteotomy guide device shown in FIG. 2 taken across the second sagittal axis B-B shown in FIG. 7.

FIG. 19 illustrates a flow chart of one embodiment of the disclosed method.

FIGS. 20 and 21 illustrate the bone spacer guide device being fixed onto a tibia. FIGS. 22 and 23 illustrate drilling of the tibia using the bone spacer guide device. FIG. 24 shows the tibia after the drilling step. FIG. 25 shows wires being inserted into the tibia. FIGS. 26 and 27 illustrate the formation of the wedge in the tibia. FIGS. 28 and 29 illustrate the bone spacer guide device being provided on the tibia. FIGS. 30 and 31 illustrate the fixation plate being affixed on the tibia.

DETAILED DESCRIPTION OF THE INVENTION

I. Overview

The embodiments described herein are directed to surgical devices and kits that include an osteotomy guide device and/or a bone spacer guide device and methods of using the surgical devices and kits. In general, the surgical kit can be used in a surgical method for correcting a misalignment of a lower limb, for example, misalignment of a knee joint, that involves performing a fibular osteotomy and/or a tibial osteotomy, and/or administering stem cells.

II. Tibial and Fibular Osteotomies

Figure 1B:
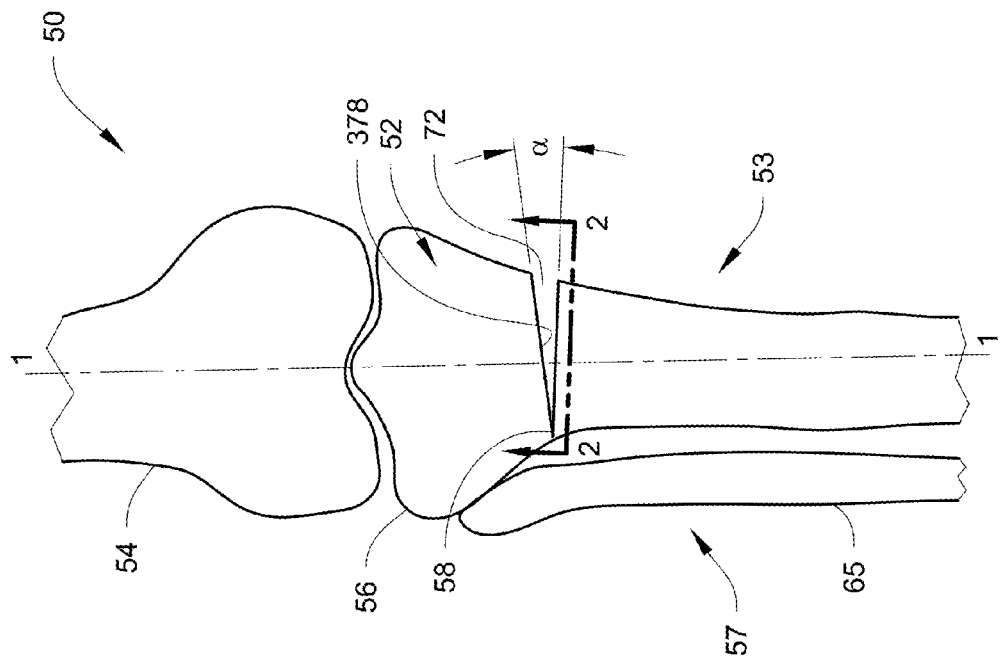
FIGS. 1A and 1B illustrate a lower limb of a patient that includes a femur and a tibia. Also illustrated are a fibular osteotomy site and a tibial osteotomy site, according to one embodiment.
Figure 1A:
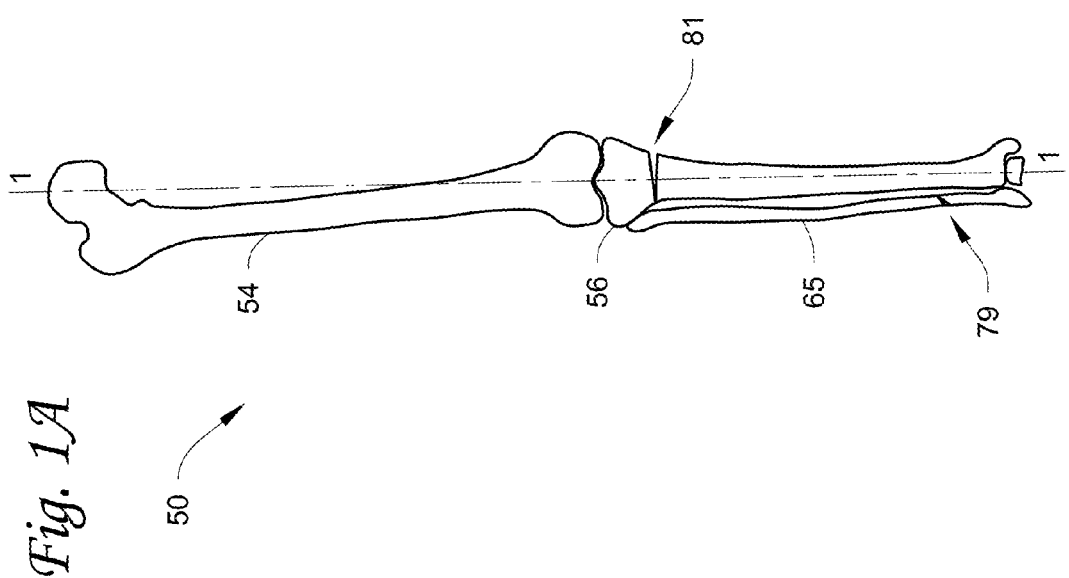

Tibial and fibular osteotomies are described with reference to FIGS. 1A and 1B, which show a lower limb 50 of a patient having a neutral axis 1-1 that includes a femur 54, a tibia 56 and a fibula 65. In some embodiments, when the lower limb 50 is misaligned with the neutral axis 1-1 due to, for example, wear and tear of the cartilage, birth defects, post-traumatic fracture, osteoarthritis or rheumatoid arthritis, a tibial osteotomy can be performed to correct such a misalignment. In some examples, a wedge opening 72 is formed in the tibia 56 when performing the tibial osteotomy. The wedge opening 72 can have a predetermined wedge angle α to correct the misalignment as illustrated in FIGS. 1A and 1B. Note that FIGS. 1A and 1B illustrate a pre-op plan of the tibial osteotomy with a predetermined wedge angle α of nine degrees to correct the misalignment of the lower limb 50, but it is to be realized that the wedge angle α necessary to correct the misalignment can be any angle that is suitable for correcting a misalignment of the lower limb, and can depend on the condition of each individual patient.

In some examples, the tibial osteotomy is performed below a tibial tuberosity 52. In general, a tibial osteotomy below the tibial tuberosity 52 is not recommended to patients. This is because tibial osteotomies above the tibial tuberosity 52 involve cutting into the cancellous bone (not shown), whereas tibial osteotomies below the tibial tuberosity 52 involves cutting into the cortical bone (not shown). It is generally accepted that the healing rates of the cortical bone is slower than that of the cancellous bone. As such, it is generally accepted that tibial osteotomies below the tibial tuberosity 52 do not result in successful union of the bone following the procedure, and is not generally recommended to relatively older patients, for example, older patients who are in the fourth decade or more of their lives.

The present inventors have found that the disclosed method that involves the use of the disclosed osteotomy guide device and/or the bone spacer guide device when performing a tibial osteotomy and/or a fibular osteotomy can lead to successful union of the bone following the procedure(s), even in older patients who are past the fourth decade of their lives. The disclosed methods also can lead to: (1) correction of misalignment: (2) regeneration of the bone in a relatively short time period as compared to that of conventional methods; (3) minimizing neurovascular bundle injury; (4) reducing stiffness in the knee after the procedure; (5) a smaller incision at the site of the respective osteotomies as compared to that of conventional methods; and (6) ease in performing the surgery; and (7) minimum disruption of the periosteum as compared to that of conventional methods which involve sawing.

III. Surgical Kit Overview

In one embodiment, the surgical kit includes an osteotomy guide device and/or a bone spacer guide device and is used for performing a tibial osteotomy and/or a fibular osteotomy. In some examples, the tibial osteotomy involves drilling of the tibia 56 through cortices (not shown) of the tibia 56. In some examples, drilling of the tibia 56 can involve the use of a drill and a cutting tool as generally known in the art. An example of a drill that can be used has the following specifications.

A power tool made by Stryker® that includes:
a. Core power console (code: 5400-050-000)
b. Core universal driver (code: 5400-099-000)
c. TPS Cord (code: 5100-0004-000)
d. Synthes® drill attachment (code 4100-110-000).

An example of a drill bit that can be used has the following specifications: diameter of 2.0 mm, length 75 mm, and 2-flute for quick coupling.

In some examples, the cutting tool utilized can be a drill bit to create, for example, drill holes in the tibia 56.

IV. Osteotomy Guide Device

Figure 2:
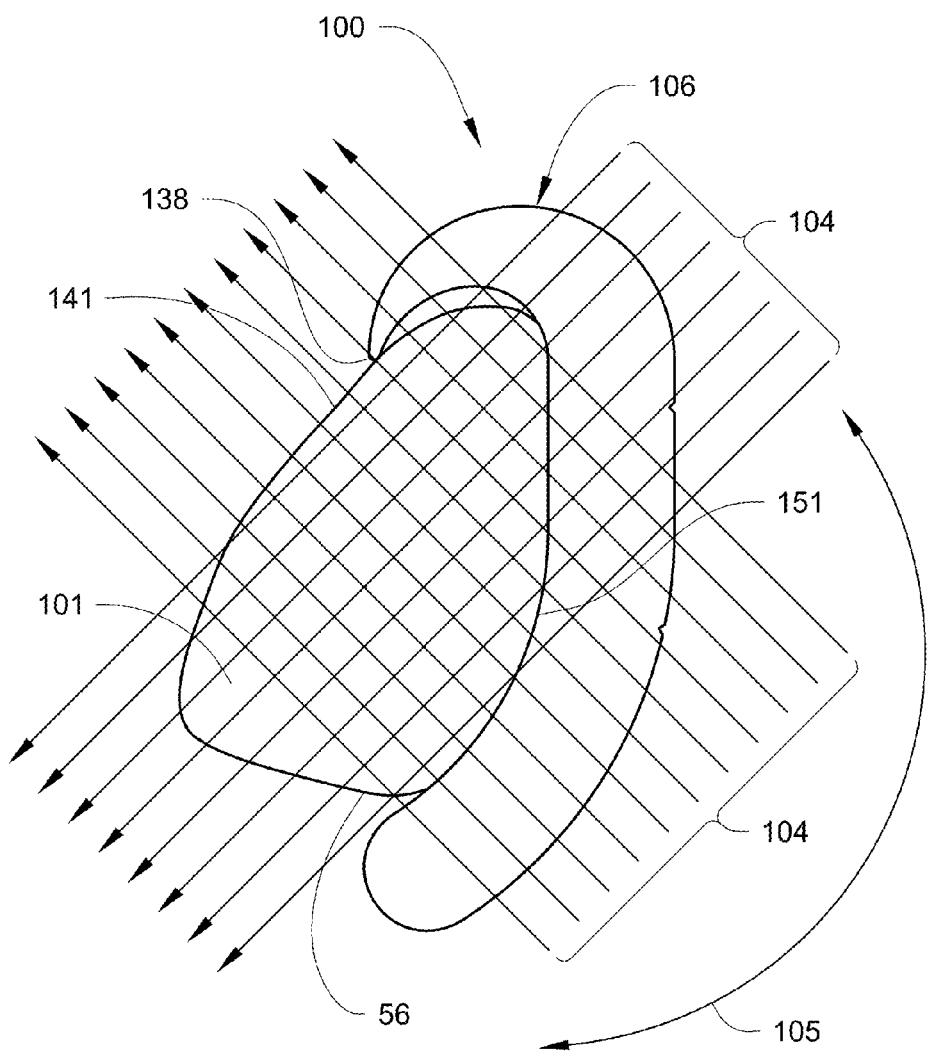
FIG. 2 illustrates a top plan view of one embodiment of an osteotomy guide device that is fixed on the tibia shown in FIGS. 1A and 1B. Note that a bottom view of the osteotomy guide device is similar to FIG. 2

FIG. 2 shows a top plan view of one embodiment of an osteotomy guide device 100 that can be included in the surgical kit. FIG. 2 also shows a cross-sectional top view taken across a horizontal axis 2-2 (see FIG. 1B) of the tibia 56, and the osteotomy guide device 100 being fixed or mounted on the tibia 56. FIG. 2 further shows arrows 104, which represent directions of the drill paths through the osteotomy guide device 100 and the tibia 56, which will be discussed in further detail below.

Generally, the osteotomy guide device 100 is configured to allow drilling to occur around the tibia 56, for example, as shown by an arrow 105 in FIG. 2, and across a horizontal cross-sectional plane 101 of the tibia 56 so that the direction of each of the drill paths, e.g., as represented by each of the arrows 104, is substantially parallel to or on the same horizontal cross-sectional plane 101 of the tibia 56. In some examples, the horizontal cross-sectional plane 101 is substantially perpendicular to the neutral axis 1-1. In some examples, the term "substantially perpendicular to the neutral axis 1-1" means that the horizontal cross-sectional plane 101 is 90±10 degrees relative to the neutral axis 1-1. In some examples, the term "the direction of each of the drill paths is substantially parallel to or on the same horizontal cross-sectional plane" means that the direction of each of the drill paths is 0±5 degrees relative to the horizontal cross-sectional plane 101. In some examples, the drilling is conducted at a tibial osteotomy site 81, where the tibial osteotomy site 81, for example, is at a high tibial area and below the tibial tuberosity 52.

Note that the directions of the drill paths represented by the arrows 104 in FIG. 2 are shown to be either substantially parallel or substantially perpendicular to one another. However, it is to be realized that the directions of the drill paths can be any direction, so long as the directions are substantially parallel to or on the same horizontal cross-sectional plane 101 of the tibia 56. In general, the osteotomy guide device 100 allows drilling around the tibia 56 to be conducted efficiently and accurately when performing the tibial osteotomy.

Further details of the osteotomy guide device 100 will now be discussed with reference to FIGS. 2 and 3. The osteotomy guide device 100 has a base 102 having a central portion 125, an upwardly extending portion 106 and a downwardly extending portion 121. In some examples, the central portion 125 is an elongated central portion that extends from a first end 109 to a second end 115, thereby defining a vertical axis 3-3 when the device 100 is viewed in top plan view. In some examples, the upwardly extending portion 106 extends upwardly from the first end 109 of the elongated central portion 125. In some examples, the downwardly extending portion 121 extends downwardly from the second end 115 of the elongated central portion 125. In some examples, the upwardly extending portion 106, the elongated central portion 125 and the downwardly extending portion 121 of the base 102 is generally continuous as shown in FIG. 3.

In some examples, the upwardly extending portion 106 is a latching portion that is in the shape of a hook. In some examples, the base 102 has an inner side 131 and an outer side 134, and the latching portion 106 hooks toward the inner side 131 of the base 102 as shown in FIG. 2. Referring to FIGS. 2 and 3, in some examples, the latching portion 106 is dimensioned so that a tip 138 of the latching portion 106 can latch onto a surface 141 of the tibia 56. In some examples, the latching portion 106 functions to fix the device 100 onto the tibia 56 so that the device 100 is in a fixed state as shown, for example, in FIG. 2. In some examples, the downwardly extending portion 121 is a flared portion that has a curvature relative to the vertical axis 3-3. In some examples, the flared portion 121 curves toward the inner side 131 of the device 100 relative to the vertical axis 3-3.

In some examples, the elongated central portion 125 and the flared portion 121 are generally continuous. In some examples, the flared portion 121 curves towards the inner side 131 such that an outline 146 of the elongated central portion 125 and the flared portion 121 as viewed in top view generally follows at least a portion of an outline 151 of the tibia 56 as viewed in top view when the device 100 is in the fixed state as shown in FIG. 2. In some examples, when the device 100 is in the fixed state, the elongated central portion 125 and/or the flared portion 121 is in contact with the surface 141 of the tibia 56. Suitably, in use, the device contacts with and is in close fit with the lateral border of the tibia. In some examples, the flared portion 121 curves at an angle β relative to the vertical axis 3-3. In some examples, the angle β is an angle that allows the outline 146 of the elongated central portion 125 and the flared portion 121 to generally follow the outline 151 of the tibia 56 when the device 100 is in the fixed state as shown in FIG. 2. In some examples, the angle β can be about 0 to about 90 degrees. In some examples, the angle β can be 0±15 to 90±15 degrees. In some examples, the angle β can be 45±15 degrees. In some examples, the angle β can be 45±10 degrees, in particular the angle can be 45±5 degrees, in particular be 45 degrees. In some examples, the central portion 125 has a width w1 and the flared portion 121 has a width w2. In some examples, w1 may be equal or different from w2. In some examples, w1 and/or w2 can be about 0.5 cm to about 2 cm. In some examples w1 can be 10 mm and w2 can be 12 mm.

With reference to FIGS. 4 and 5, the base 102 has a thickness h and a length L, and includes a plurality of passageways 161 that are formed through the thickness h of the base 102. In some examples, the thickness h is about 0.5 cm to about 5 cm. In some examples, the length L is about 60 mm to about 80 mm. Note that these values are only exemplary and can vary depending on, for example, a size of the tibia of the patient, the condition of the patient, etc.

In some examples, the plurality of passageways 161 include passageways 168 that are adapted for positioning a direction of the drilling. The term "passageways that are adapted for positioning the direction of the drilling" means that the passageways have a structure that allows a cutting tool, for example, a drill bit, to pass through each of the passageways so that drilling can occur in the direction of each of the respective passageways.

With reference to FIGS. 4-6, in some examples, the passageways 168 have respective inlets 172 and outlets 175, and the passageways 168 extend from the respective inlets 172 and the outlets 175 through the thickness h of the base 102. In some examples, the inlets 172 are provided on the outer side 134 of the device 100 while the outlets 175 are provided on the inner side 131 of the device 100. In some instances, the inlets 172 and the outlets 175 are provided along a median axis C-C of the base 102. The median axis C-C is an axis that is substantially parallel to a median plane 179 of the base 102. The median plane 179 is a plane that divides the base 102 into substantially two equal sides, one on a left side 182 of the median plane 179 and the other on a right side 184 of the median plane 179, so that a thickness h1 on the left side 182 of the median plane 179 and a thickness h2 on the right side 184 of the median plane 179 are substantially equal to one another.

Generally, each of the passageways 168 extend from each of the respective inlets 172 to each of the respective outlets 175 in a direction that is substantially parallel to or on the horizontal cross-sectional plane 101 of the tibia 56 so that drilling can occur in a direction that is substantially parallel to or on the horizontal cross-sectional plane 101 of the tibia 56.

Note that the dimensions, the number, and the positions of the passageways 168 can be any dimensions, any number and any positions that are suitable for allowing a cutting tool to pass through and position the direction of the drilling. In some examples, the base 102 can include about 3 to about 60 passageways 168. In some examples, each of the passageways 168 can have a diameter of about 0.5 mm to about 8 mm. In some examples, each of the passageways 168 can be spaced apart in about 1 mm to about 5 mm intervals. In some examples the passageways can have a diameter of about 2 to 3 mm, suitably 2.1, 2.3, 2.5 mm. In some examples the spaces between the passageways can be in the range 1 to 2 mm, suitably 1.5 to 2 mm, more suitably 1.9 mm. In some examples, the plurality of passageways 161 further includes one or more passageways 192 that is adapted for inserting and/or positioning a stabilizing member, e.g., a wire, a pin or a screw, that is suitable for use during an osteotomy. In some examples, the stabilizing member is a wire or a pin that is configured for fixation during osteotomy, e.g., a Kirschner wire (k-wire).

Details of the passageways 192 will now be described with reference to FIGS. 7-9. In some examples, the passageways 192 have inlets 202 and outlets 205. In some examples, the inlets 202 are provided on the outer side 134 of the base 102 while the outlets 205 are provided on the inner side 131 of the base 102. In some instances, the inlets 202 and the outlets 205 are provided along a first sagittal axis A-A and/or a second sagittal axis B-B of the base 102, which are substantially parallel to the median axis C-C shown in FIG. 5.

Generally, each of the inlets 202 is configured to receive a wire, pin or screw, e.g., a K-wire, and each of respective passageways 192 is configured to allow the wire, pin or screw to pass through each of the respective passageways 192 and exit out of each of the respective outlets 205. In some examples, each of the passageways 192 is configured so as to allow the wire, pin or screw to help fix and/or stabilize the device 100 on the tibia 56.

Note that the dimensions, the number and the positions of the passageways 192 can be any dimensions, any number and any positions that are suitable for allowing a wire, pin or screw to pass through the base 102 and allow the wire, pin or screw to help fix and/or stabilize the device 100 on the tibia 56. In some examples, the base 102 can include about 3 to about 60 passageways 192. In some examples, each of the passageways 192 can have a diameter of about 0.5 mm to about 8 mm. In some examples, each of the passageways 192 can be spaced apart in about 1 mm to about 5 mm intervals.

In some examples, the plurality of passageways 161 further includes one or more passageways 194 that is adapted for connecting a handle, for example, a butterfly screw. Details of an example of a handle that can be used will be discussed below.

In some examples, the passageways 194 have inlets 302 and outlets 305. In some examples, the inlets 302 are provided on the outer side 134 of the base 102 while the outlets 305 are provided on the inner side 131 of the base 102. In some instances, the inlets 302 and the outlets 305 are provided along the first sagittal axis A-A and/or the second sagittal axis B-B of the base 102, which are substantially parallel to the median axis C-C shown in FIG. 5.

Generally, each of the inlets 302 is configured to receive a handle, e.g., a butterfly screw, and each of the respective passageways 194 is configured to allow the handle to engage with the device 100 as described, for example, in detail below. In some examples, each of the passageways 194 is configured so as to allow a user to handle the device 100.

Note that the osteotomy guide device 100 can be made of any material that is suitable for use in drilling through a tibia when performing a tibial osteotomy. The material can include, but is not limited to, metal.

V. Handle

Figure 10:
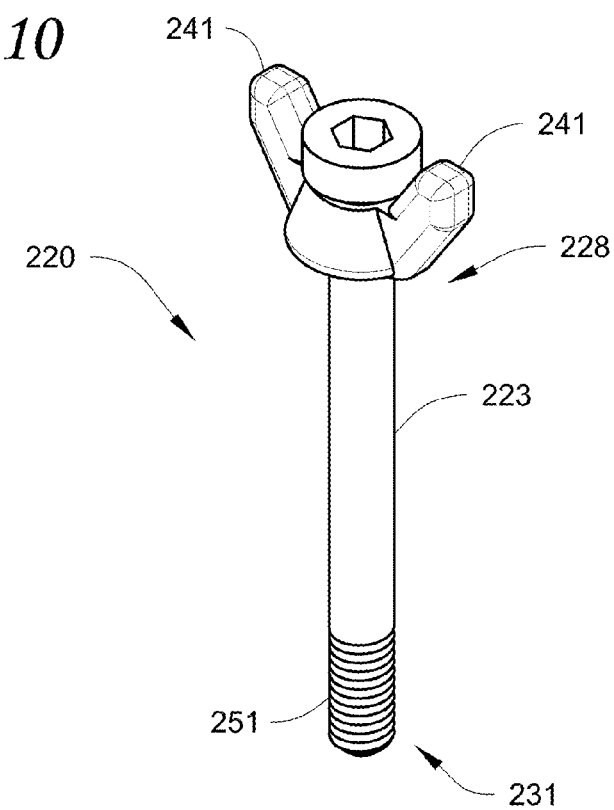
FIG. 10 illustrates a perspective view of one embodiment of a handle that can be connected to the osteotomy guide device shown in FIG. 2.
Figure 11:
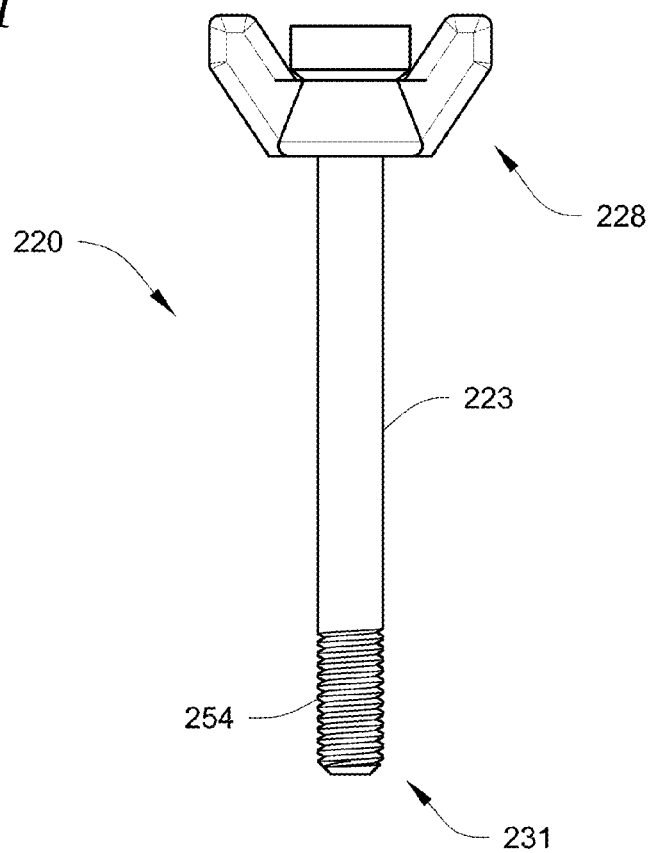
FIG. 11 illustrates a side view of the handle shown in FIG. 10.
Figure 12:
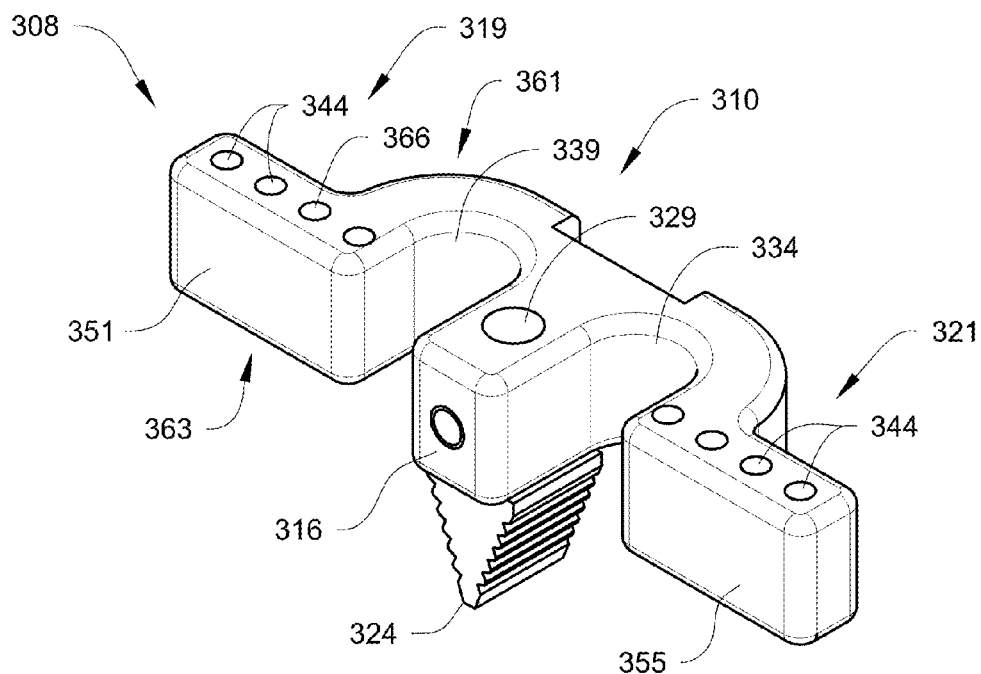
FIG. 12 illustrates a perspective of one embodiment of a bone spacer guide device.
Figure 13:
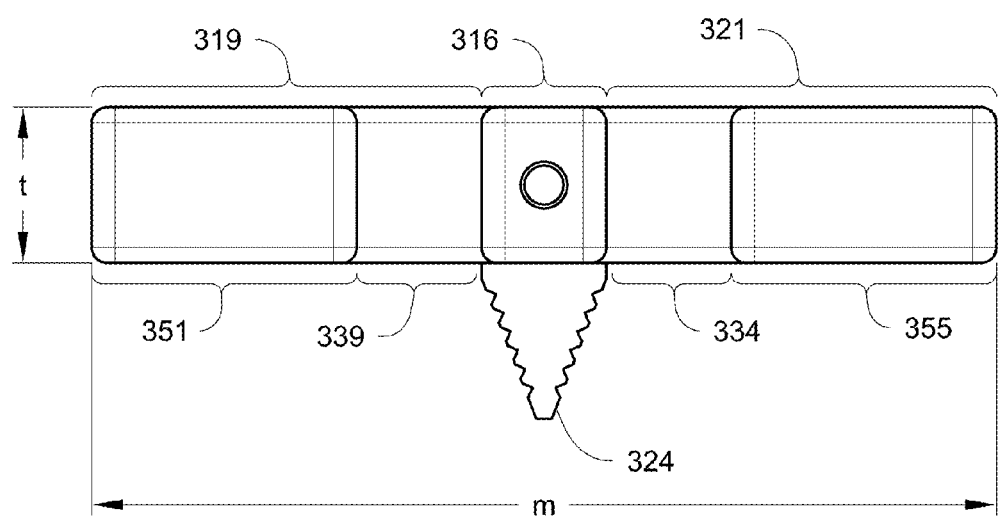
FIG. 13 illustrates a side view of the bone spacer guide device shown in FIG. 12.

FIGS. 10 and 11 show one example of a handle 220 that can be connected to the device 100 via the passageway 194. The handle 220 is an elongated member 223 having a first end 228 and a second end 231. The first end 228 has a gripping portion 241 that is in the shape of a dovetail and the second end 231 has a connecting portion 251 that includes threads 254 for gripping corresponding threads. In some examples, internal threads (not shown) that can grip the threads 254 of the handle 220 are provided in one or more of the passageways 194 so as to engage the handle 220 with the device 100.

Note that the handle that can be used with the device 100 is not limited to the handle 220 illustrated in FIGS. 10-11, and can be any handle that is suitable for connecting with one or more of the passageways 194 and handling the device 100.

Note also that the handle 220 can be made of any material that is suitable for use in positioning the osteotomy guide device 100. The material can include, but is not limited to, metal.

VI. Bone Spacer Guide Device

In one embodiment, the surgical kit further includes a bone spacer guide device. Generally, the bone spacer guide device is used to maintain a desired angle of a wedge opening 72 that is produced during the tibial osteotomy, for example, while a fixation plate is affixed on the tibia 56 (refer to FIG. 1B).

FIGS. 12-18 show one embodiment of a bone spacer guide device 308 included in the surgical kit. The device 308 has a main body 310 having an upper side 361, a lower side 363, a thickness t and a length m. In some examples, the thickness t is about 0.1 cm to about 10 cm, and the length m can be about 2 cm to about 20 cm. Note that these values are exemplary only, and can vary depending on, for example, a size of the tibia 56, the condition of the patient, etc. In some examples, the length m can be about 5 to 6 cm, suitably 5.8 cm and t can be about 1 cm. The main body 310 includes a central portion 316 with two opposing side portions 319, 321 that extend outwardly in a horizontal direction from the central portion 316. The central portion 316 has a wedge member 324 that extends downwardly towards the lower side 363. In some examples, the wedge member 324 can be detached from the main body 310, as will be discussed further in detail below.

Figure 14:
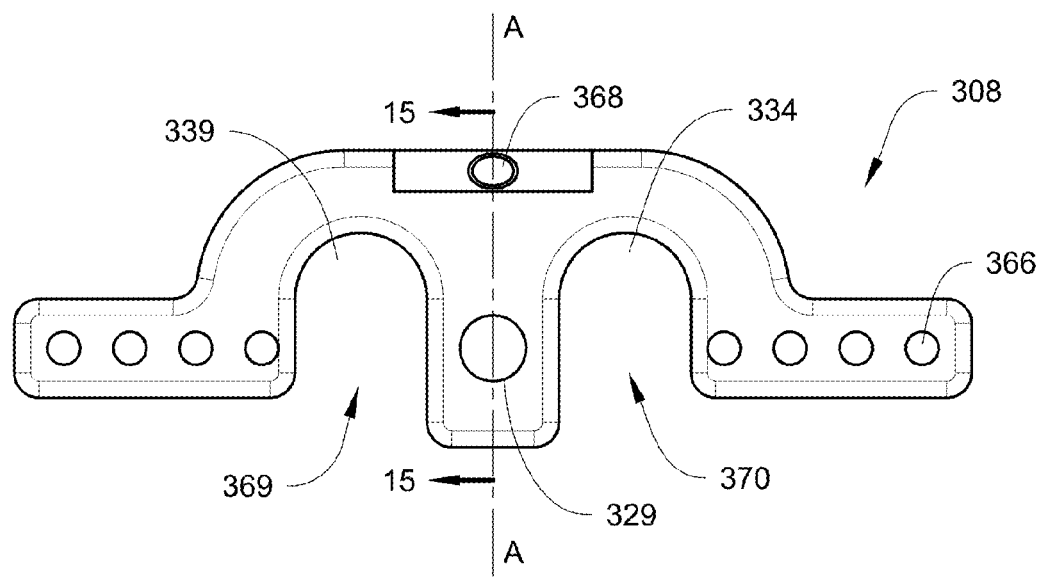
FIG. 14 illustrates a top view of the bone spacer guide device shown in FIG. 12. Note that a bottom view of the bone spacer guide device is similar to FIG. 14.
Figure 15:
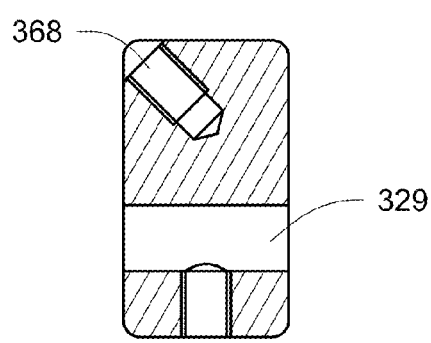
FIG. 15 illustrates a cross-sectional side view of the bone spacer guide shown in FIG. 14 taken across the axis A-A shown in FIG. 14.

In some examples, the side portion 319 can include a groove portion 339 adjacent the central portion 316, and an arm portion 351 that extends outwardly in a horizontal direction from the groove portion 339. The side portion 321 has a structure that can be similar to that of the side portion 319, and can include a groove portion 334 and an arm portion 355 that extends outwardly from the groove portion 334. Each of the groove portions 334, 339 can be generally C-shaped or U-shaped as viewed in top view, as shown in FIG. 14.

In some examples, each of the arm portions 351, 355 includes one or more passageways 344 that has an inlet 366 on the upper side 361 and a corresponding outlet (not shown) on the lower side 363. Each of the passageways 344 extend from the inlet 366 to the corresponding outlet through the thickness t of the main body 310.

Generally, the inlet 366 is configured to receive a stabilizing member, e.g., a wire or a pin such as a k-wire, and each of the respective passageways 344 is configured to allow the wire, pin or screw to pass through each of the respective passageways 344 and exit out of each of the respective outlets. In some examples, each of the passageways 344 is configured so as to allow the wire, pin or screw to help fix and/or stabilize the device 308 on the tibia 56.

Note that the dimensions, the number and the positions of the passageways 344 can be any dimensions, any number and any positions that are suitable for allowing a wire, pin or screw to pass through the main body 310 and allow the wire, pin or screw to help fix and/or stabilize the device 308 on the tibia 56. In some examples, the main body 310 can include about 1 to about 20 passageways 344. In some examples, each of the passageways 344 can have a diameter of about 0.2 mm to about 10 mm. In some examples, each of the passageways 344 can be spaced apart in about 1 mm to about 5 mm intervals. In some examples, each of the arm portions 351, 355 include four passageways 344. The passageways can be spaced apart by around 4 mm.

In some examples, the central portion 316 includes an opening 368 on the upper side 361 of the device 308. In some examples, the opening 368 is configured to receive a handle, for example, the handle 220, so that the handle 220 can be connected to the device 308. In some examples, the opening 368 includes internal threads (not shown) that can grip the threads 254 of the handle 220 so as to engage the handle 220 with the device 308.

Note that the handle that can be used with the device 308 is not limited to the handle 220 illustrated in FIGS. 10-11, and can be any handle that is suitable for connecting with the opening 368 and handling the device 308.

Wedge Member

Figure 16:
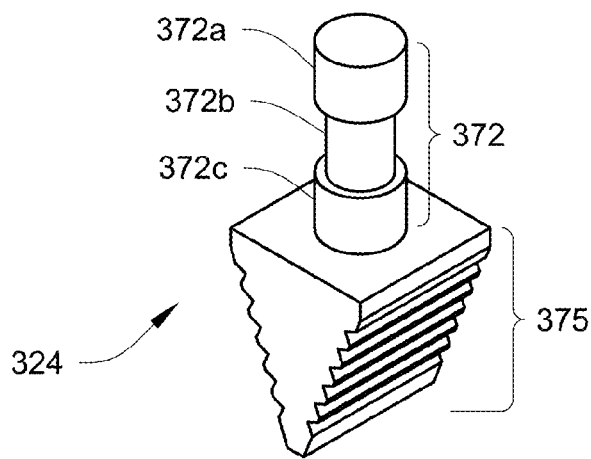
FIG. 16 illustrates one embodiment of a wedge member that can be detachably connected to the bone spacer guide device shown in FIG. 12.

As mentioned above, in some examples, the wedge member 324 can be detached from the main body 310. FIG. 16 shows one example of the wedge member 324 that is detached from the main body 310. The wedge member 324 includes an attaching portion 372 and a wedge portion 375. The attaching portion 372 is generally cylindrical in shape, and has an upper cylindrical portion 372a, a central cylindrical portion 372b, and a lower cylindrical portion 372c. A diameter of the central cylindrical portion 372b is smaller than each of the diameters of the upper and lower cylindrical portions 372a, 372c. The attaching portion 372 can be inserted through a passageway 329 that is formed through the thickness t of the central portion 316. Note that the attaching portion 372 shown in FIG. 16 shows three separate portions where the central cylindrical portion 372b has a smaller diameter, but it is to be realized that the cylindrically shaped attaching portion 372 can have one constant diameter such that it is not divided into different portions. Note also, that the attaching portion 372 can be any shape that is suitable for attaching the wedge member 324 to the main body 310. In some examples, the wedge, suitably a triangular prism, can be about 4 to 12 mm, suitably 8 mm in width at a first (thick) end of the wedge and taper to 0.5 to 3 mm, suitably 1 mm at the second end (thin) end of the wedge. The distance between the base rectangle and apex edge (first to second end) can be about 5 to 20 mm, suitably 10 mm. The apex edge length can be about 5 to 20 mm, suitably 8 mm.

Figure 17:
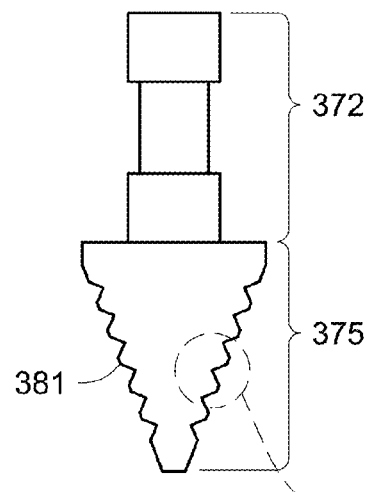
FIG. 17 illustrates a side view of the wedge member shown in FIG. 16.
Figure 18:
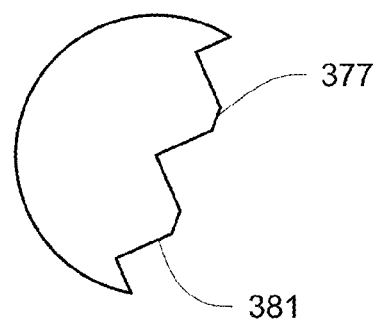
FIG. 18 illustrates an exploded view of a portion A shown in FIG. 17.

In some examples, a surface 377 of the wedge portion 375 has ridges 381 as shown in FIGS. 17 and 18. In some examples, the ridges 381 are configured to provide a grip with a surface 378 (see FIG. 1B) of the wedge opening 72 when the wedge portion 375 is inserted into the wedge opening 72, as described in detail in section VII. Note that while FIGS. 16-18 show the surface 377 having ridges 381, it is to be realized that the surface can have any suitable texture for insertion of the wedge portion 375 into the wedge opening including, but not limited to, a smooth surface and/or ridges.

Note also that the bone spacer guide device 308 can be made of any material that is suitable for maintaining the predetermined wedge angle α of the wedge opening 72 that is formed during the tibial osteotomy, for example, while a fixation plate is affixed on the tibia 56. The material can include, but is not limited to, metal or a polymer.

VII. Method of Using Osteotomy Guide Device and/or Bone Spacer Guide Device

One embodiment of the method using the osteotomy guide tool 100 and/or the bone spacer guide tool 310 will now be described. In some examples, the method generally involves performing both tibial and fibular osteotomies. The tibial osteotomy generally can involve drilling along at least a portion of the outline 151 of the tibia 56 as viewed in top plan view at the tibial osteotomy site 81 (see FIG. 1A), where the drilling can occur across a horizontal cross-sectional plane 101 of the tibia 56 so that the direction of each of the drill paths is substantially parallel to or on the horizontal cross-sectional plane 101 of the tibia 56. The fibular osteotomy can performed at a fibular osteotomy site 79 (see FIG. 1A), for example, at a distal third position of the fibula 65 as is generally known in the art. In some examples, the fibular osteotomy can be conducted at approximately 45±15 degrees relative to the neutral axis 1-1.

FIG. 19 shows a flow chart of one example of a method 400 of using the osteotomy guide tool 100 and/or the bone spacer guide tool 310. The method 400 begins by making an incision at the tibial osteotomy site 81 (see FIG. 1A) where the wedge opening 72 is to be formed in the tibia 56 (404). After the incision is made, the osteotomy guide device 100 is fixed on the tibia 56 at the site where the wedge opening 72 is to be formed so as to be in a fixed state (409).

Figure 20:
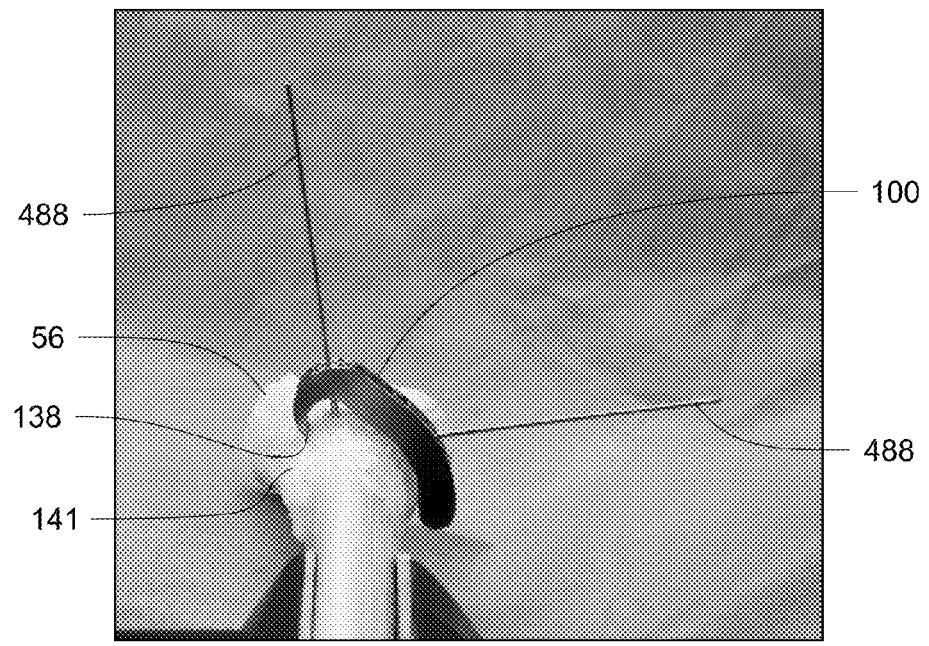
FIGS. 20-31 show photos of a model that is reflective of the various steps in the disclosed method shown in FIG. 19.

Referring to FIGS. 1A, 2, 5 and 20-21, in one example, the osteotomy guide device 100 is fixed on the tibia 56 by latching the tip 138 of the device 100 on the surface 141 of the tibia 56. In some examples, the handle 220 can be inserted in the passageway 194 to help position the device 100 on the tibia 56. The osteotomy guide device 100 is positioned at the tibial osteotomy site 81 where the wedge opening 72 is to be formed, and so that the median axis C-C is substantially parallel to the horizontal cross-sectional plane 101 of the tibia 56. In some examples, the osteotomy guide device 100 is positioned so that at least a part of the central portion 125 and/or the flared portion 121 is in contact with the surface of the tibia 141 as shown in FIGS. 2 and 20. When the osteotomy guide device 100 is in the fixed state as shown in FIGS. 2 and 20, drilling can be performed along at least a portion of the outline 151 of the tibia 56, where the drilling occurs across the horizontal cross-sectional plane 101 of the tibia 56 so that the direction of each of the drill paths is substantially parallel to or on the same horizontal cross-sectional plane 101 of the tibia 56.

Figure 21:
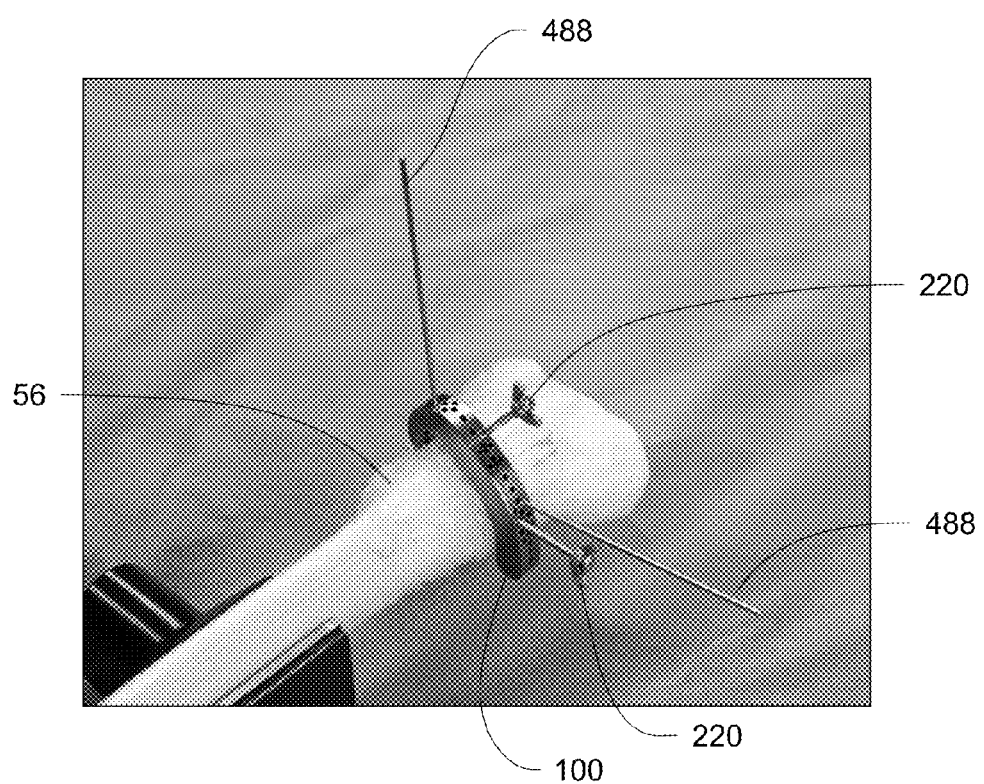

After 409, the osteotomy guide device is stabilized using, for example, stabilizing members 488, for example, wires or a pins (415). The wires or pins 488 can be k-wires. Referring to FIGS. 7, 20 and 21, in some examples, the wires or pins 488 are inserted through the passageways 192 of the device 100 so as to stabilize the position of the device 100 on the tibia 56.

Figure 22:
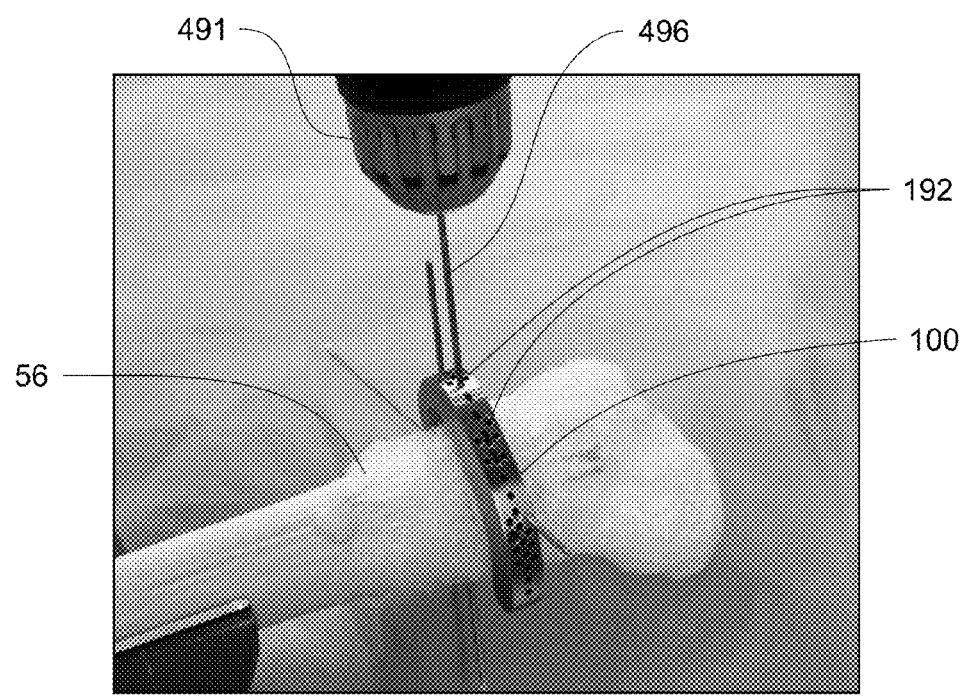
Figure 23:
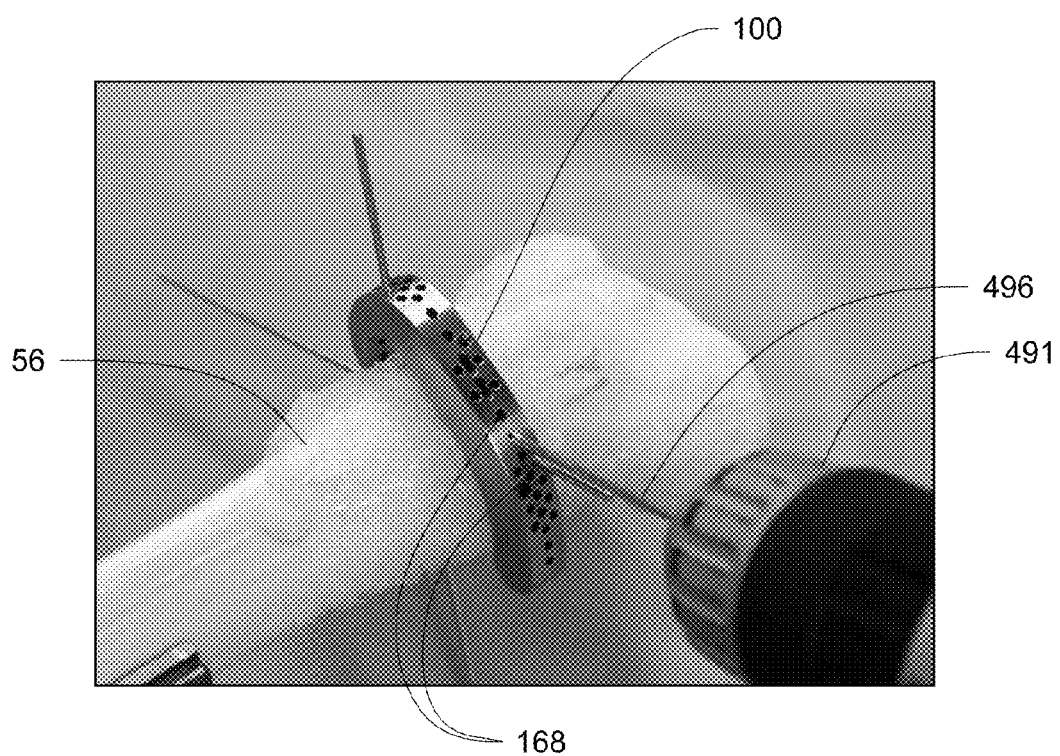

Then, at 421, drilling is conducted through the passageways 168 of the device. Referring to FIGS. 22 and 23, in some examples, a drill 491 that has a cutting tool 496, for example, a drill bit, can be used. An example of a drill that can be used has the following specifications.

A power tool made by Stryker@ that includes:
  a. Core power console (code: 5400-050-000)
  b. Core universal driver (code: 5400-099-000)
  c. TPS Cord (code: 5100-0004-000)
  d. Synthes® drill attachment (code 4100-110-000).

An example of a drill bit that can be used has the following specifications: diameter of 2.0 mm, length 75 mm, and 2-flute for quick coupling.

Referring to FIGS. 2, 5 and 22-23, the drilling can be conducted through each of the passageways 168 that is provided along the median axis C-C so that drilling can occur around the tibia 56, and across the horizontal cross-sectional plane 101 of the tibia 56 so that the direction of each of the drill paths is substantially parallel to or on the same horizontal cross-sectional plane 101 of the tibia 56. In some examples, the drilling can be conducted from a medial side 53 (see FIG. 1B) to a lateral side 57 (see FIG. 1B), for example, depending on whether drilling is being conducted on a right or left lower limb. In some examples, the drilling is conducted on a patient that requires correction of a varus deformity.

Figure 24:
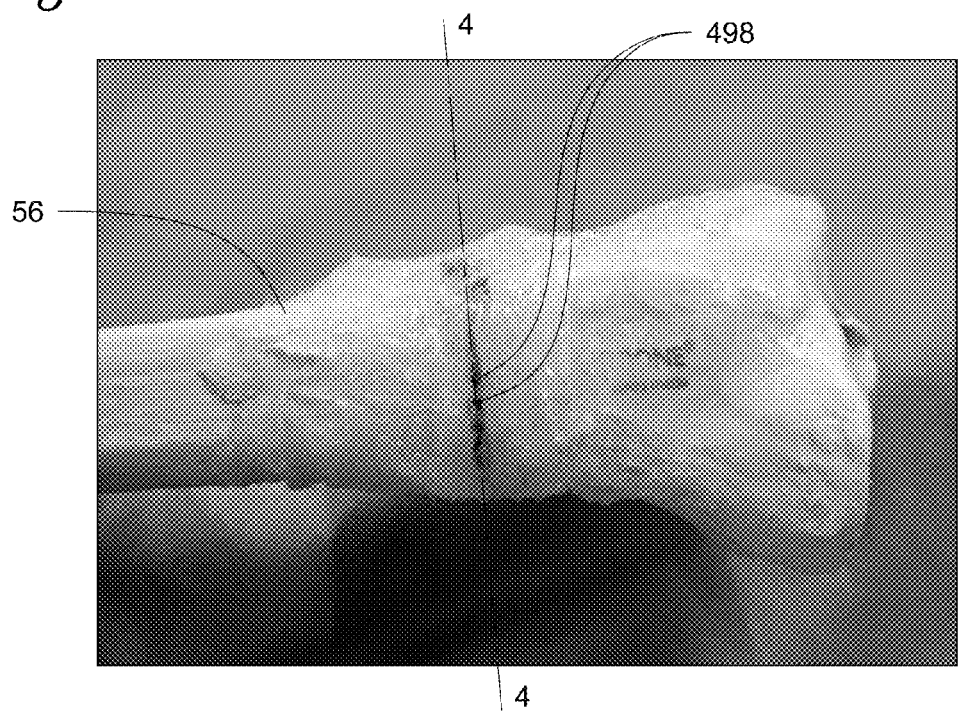

Then, at 425, the osteotomy guide device 425 is removed from the tibia 56. FIG. 24 shows drill holes 498 that are formed as a result of the drilling in step 421. Note that the drill holes 498 are aligned on an axis 4-4 that is substantially parallel to or on the horizontal cross-sectional plane 101 of the tibia 56. In some examples, the horizontal cross-sectional plane 101 is substantially perpendicular to the neutral axis 1-1 so that each of the directions of the drill holes that is formed is substantially perpendicular to the neutral axis 1-1.

Figure 25:
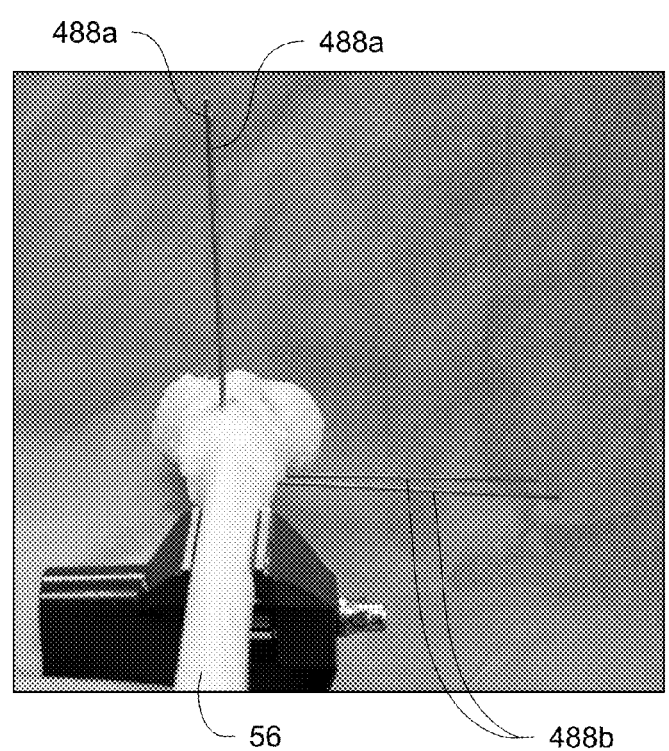

At 429, the stabilizing members 488 are inserted into the tibia 56. In the example illustrated in FIG. 25, two k-wires 488a are inserted in a direction that is perpendicular to the neutral axis 1-1 (see FIG. 1A), and two other k-wires 488b are inserted in a direction that is perpendicular to the direction of insertion of the two-wires 488a. For each pair of the k-wires 488a, 488b, each of the k-wires 488a, 488b is inserted at each side of the axis 4-4 at a corresponding location. Each of the two k-wires 488a is parallel to one another, and each of the two k-wires 488b is parallel to one another. In some examples, the k-wires 488a and/or the k-wires 488b function as a guide to avoid and/or at least reduce mal-rotation and angular deformity relative to the neutral axis 1-1 during the osteotomy process.

At 432, the tibia 56 is cracked open along the drill holes 498 so as to form the wedge opening 72. Note that FIGS. 1A and 1B show a left limb and a hinge 58 of the wedge opening 72 is shown to be on the lateral side 57. Note that for a correction done on a right limb, the wedge opening would be a mirror image of the wedge opening 72 shown in FIG. 1B. In some examples, the wedge opening 72 can be formed using procedures generally known in the art. For example, the drill holes 498 can be connected to create an osteotomy. In some examples, an x-ray of the tibia 56 taken beforehand can be used to check the position of the osteotomy.

Figure 26:
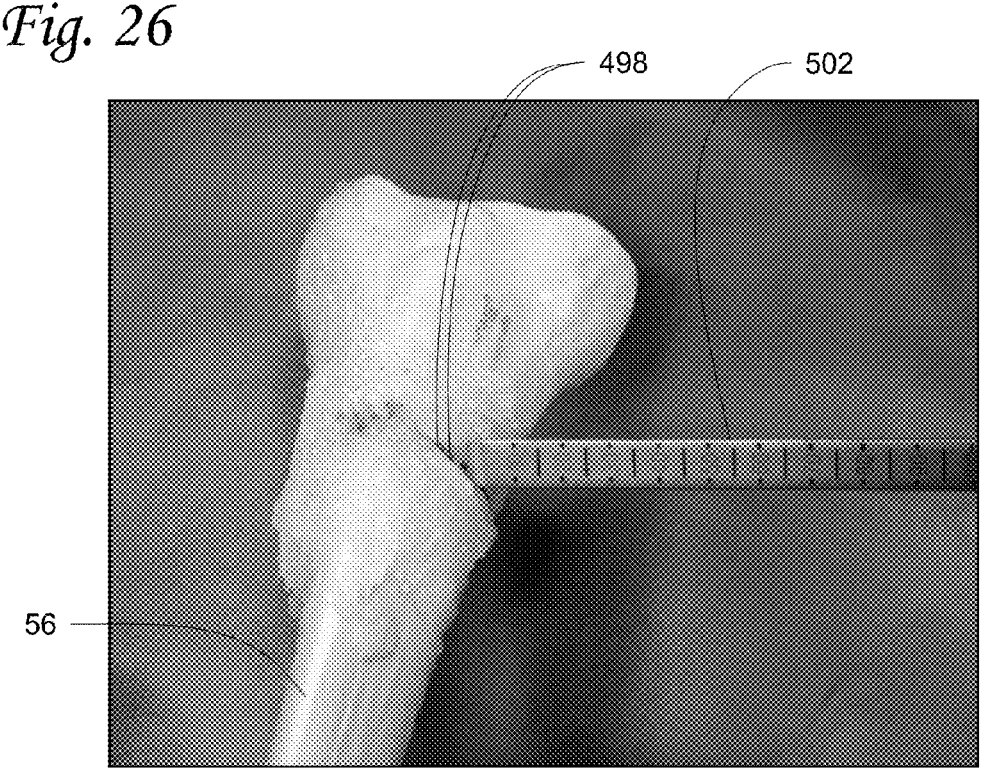

In some examples, the osteotomy can be formed using an osteotome or bone chisel 502 as shown in FIG. 26. The osteotome or bone chisel 502 that is used can be any osteotome or bone chisel suitable for use when performing an osteotomy. An example of an osteotome or bone spreader that can be used has the following specifications.

An osteotome made by TomoFix™ having the following configurations:
  a) Chisel, width 10 mm (code: 397.992)
  b) Chisel width 15 mm (code 397.993)
  c) Chisel width 20 mm (code 397.994)
  d) Chisel width 25 mm (code 397.995).

In some examples, an angular bone spreader 505 can be inserted into the opening. The angular bone spreader 505 that can be used can be any angular bone spreader that is conventionally used when performing an osteotomy. An example of an angular bone spreader 505 that can be used has the following specifications.

An angular bone spreader made by Synthes® with soft lock width of 8 mm and length of 220 mm (code: 399.097).

Figure 27:
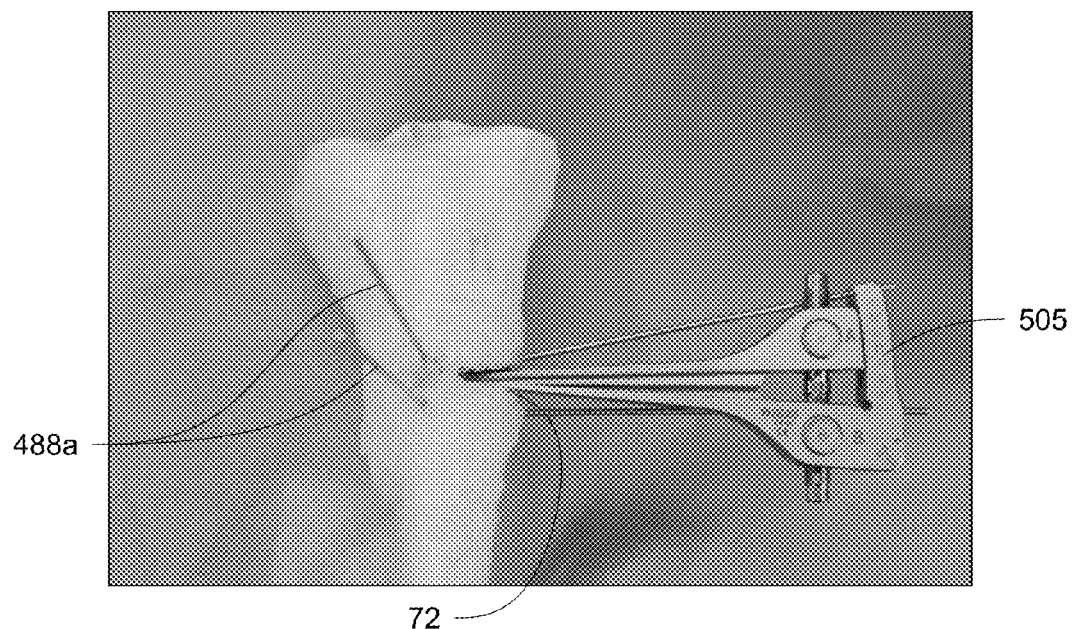

The angular bone spreader 505 then can be used to crank open the opening so as to form the wedge opening 72 (see FIG. 27). In some examples, the angular bone spreader 505 can be used to open the wedge opening 72 to the predetermined wedge angle α.

Then, at 438, the alignment of the wedge opening 72 and the wedge angle α can be checked with reference to the x-ray of the tibia 56 and/or the two pairs of k-wires 488a, 488b. In some examples, the two pairs of k-wires 488a, 488b can be checked to determine whether they are maintaining a perpendicular position relative to one another.

Figure 28:
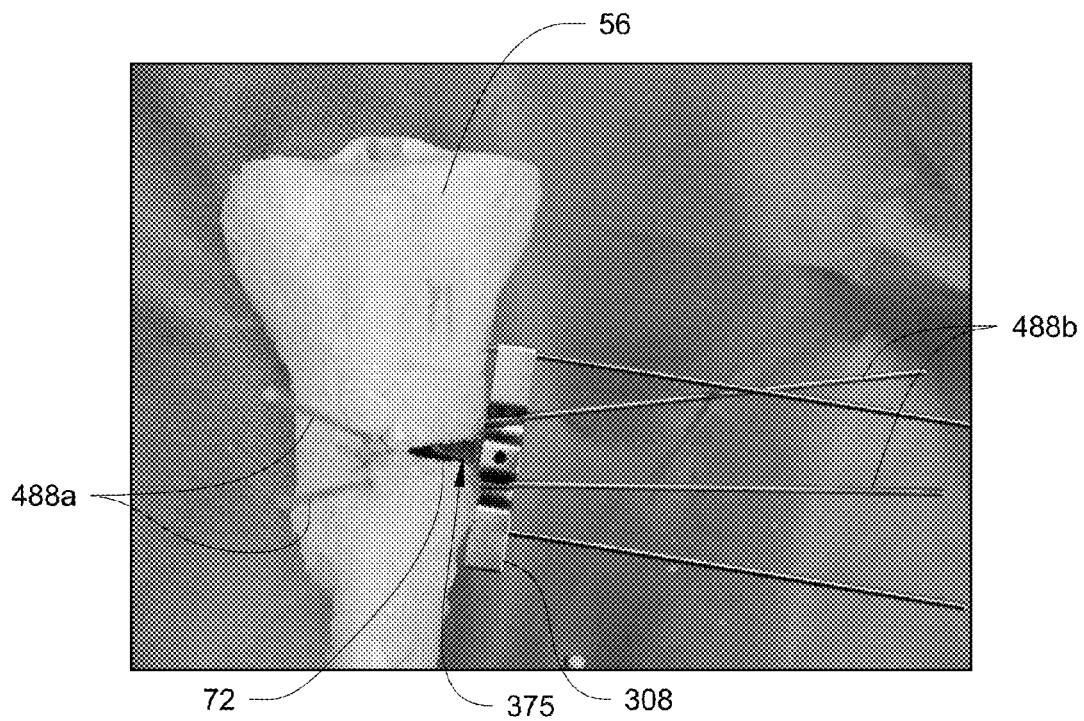
Figure 29:
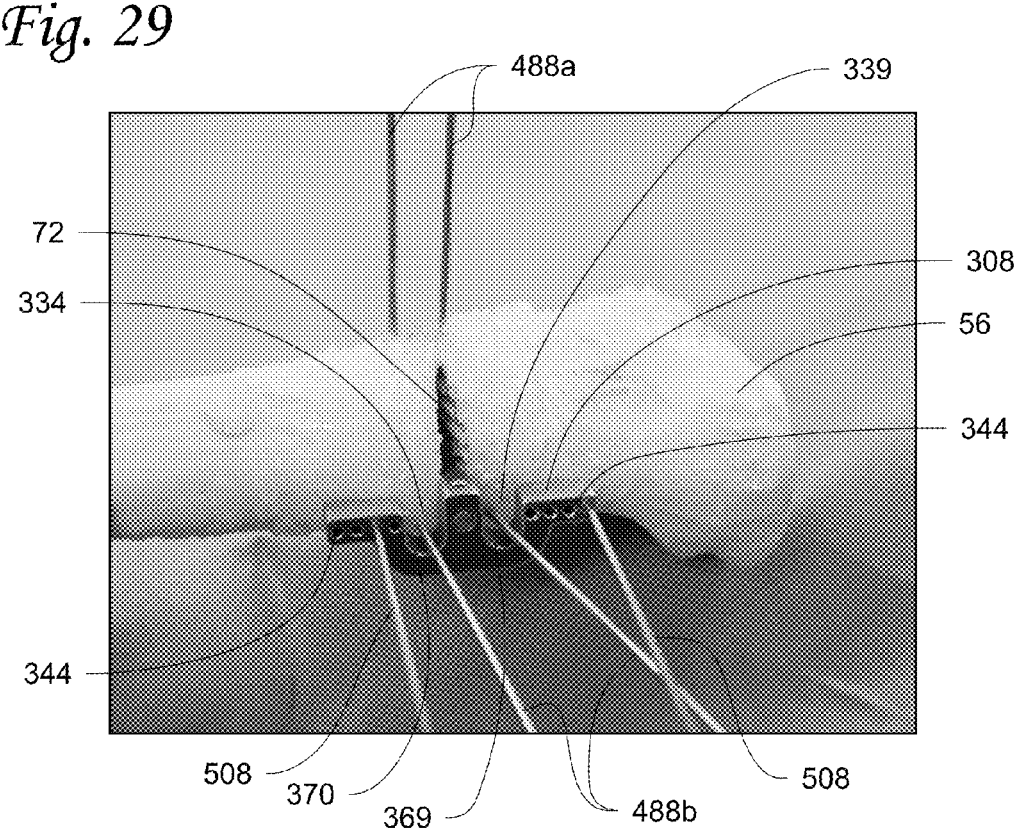

Then, at 443, the bone spacer guide device 308 can be provided on the tibia 56. With reference to FIGS. 28 and 29, generally, the bone spacer guide device 308 is provided on the tibia 56 to maintain the wedge angle α. In some examples, the bone spacer guide device 308 can be provided on the tibia 56 by inserting the wedge portion 375 into the wedge opening 72. In some examples, the bone spacer guide device 308 is positioned so that each of the k-wires 488b is provided in an opening 369, 370 of the respective groove portions 334, 339 of the device 308.

Then, at 447, additional stabilizing members 508, for examples, wires, pins or screws, are inserted through the passageways 344 of the device 308 so as to stabilize the device 308 on the tibia 56. The stabilizing members 508 can be k-wires.

Figure 30:
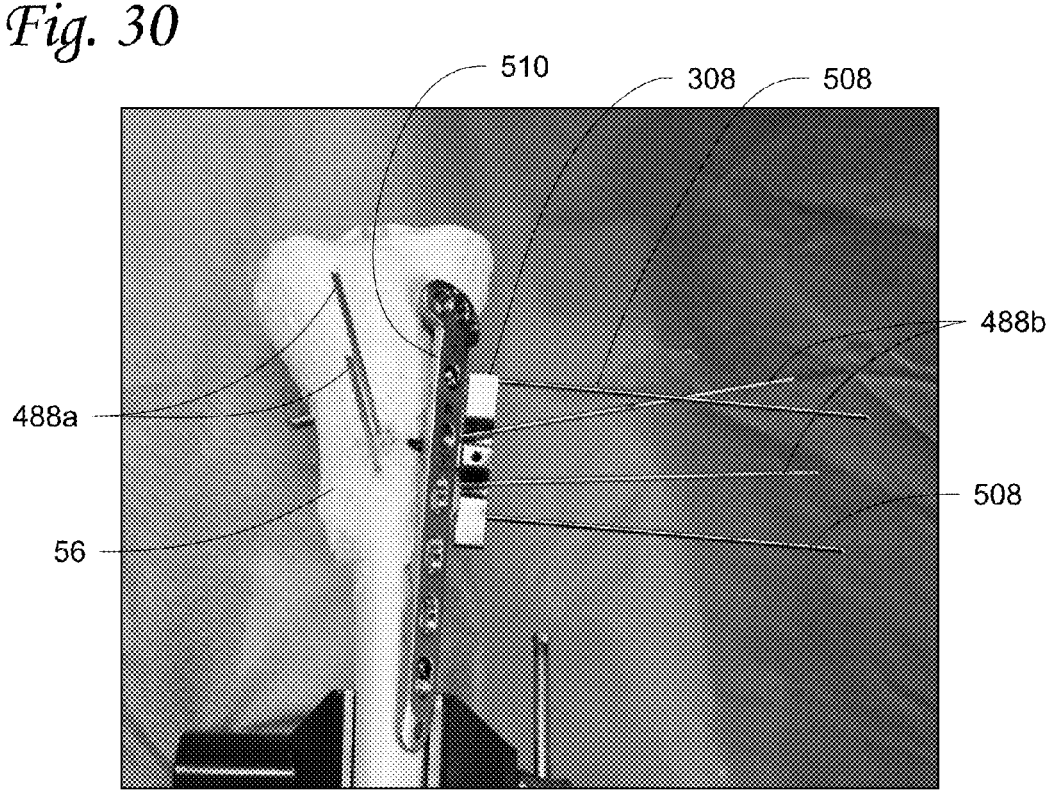
Figure 31:
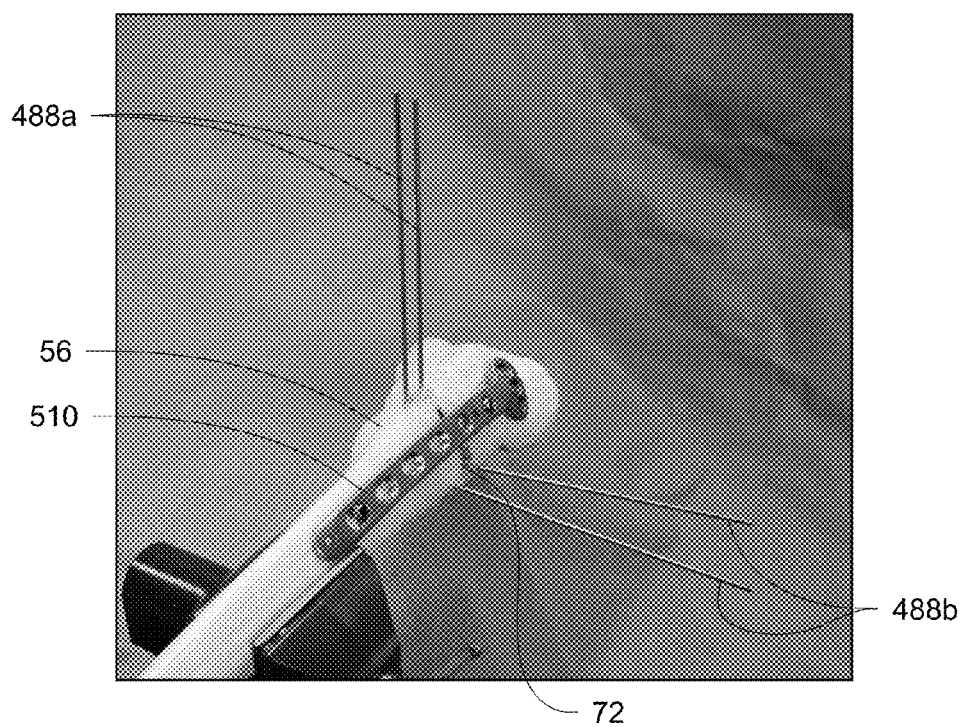

Then, at 452, a fixation plate 510 is affixed to the tibia 56 so as to maintain the wedge angle α (see FIGS. 30 and 31). The fixation plate 510 that can be used can be any fixation plate that is typically used when performing an osteotomy or any plate that can be used to hold a fracture. An example of a fixation plate 510 can have the following specifications.

LCP medial proximal tibial plate 4.5 having 6 to 12 holes, a length of 142 mm and made of pure titanium.

In some examples, the position of the fixation plate 510 can be checked with reference to the x-ray of the tibia 56.

Then, at 457, the two pairs of k-wires 488a, 488b can be checked to determine whether they are maintaining a perpendicular position relative to one another. Note that the k-wires 488b may diverge from one another due to the formation of the wedge opening 72 (see FIG. 31).

Then, at 463, the bone spacer guide device 308, the k-wires 488a, 488b and 508 are removed, and the wound is closed, for example, by suturing as generally known in the art.

Then, at 469, a fibular osteotomy 469 is performed at the fibular osteotomy site 79, for example, at a distal third position of the fibula 65 (see FIG. 1A) as is generally known in the art. In some examples, the fibular osteotomy is conducted at approximately 45±15 degrees relative to the neutral axis 1-1. Note that the fibular osteotomy 469 can be performed at any time during the method 400, and is not limited to before or after performing the tibial osteotomy.

Then, at 473, stem cells that were previously harvested are injected into the tibial osteotomy site 81 and/or the fibular osteotomy site 79. In some examples, the stem cells are harvested seven days prior to when the method 400 is performed. In some examples, the stem cells used can be, for example, peripheral blood stem cells (PBSCs). In some examples, the PBSCs are autologous. In some examples, the PBSCs are positive for CD34. In some examples, the stem cells are injected in an amount sufficient to repair the osteotomy site 79, 81 so that there is successful union of the bone at the osteotomy site 79, 81. In some examples, the effective amount of stem cells can be about $0.2\pm0.1\times10^{6\pm1}$ to about $8\pm1\times10^{6\pm2}$ of stem cells.

Harvesting and Storing Stem Cells

Figure 32:
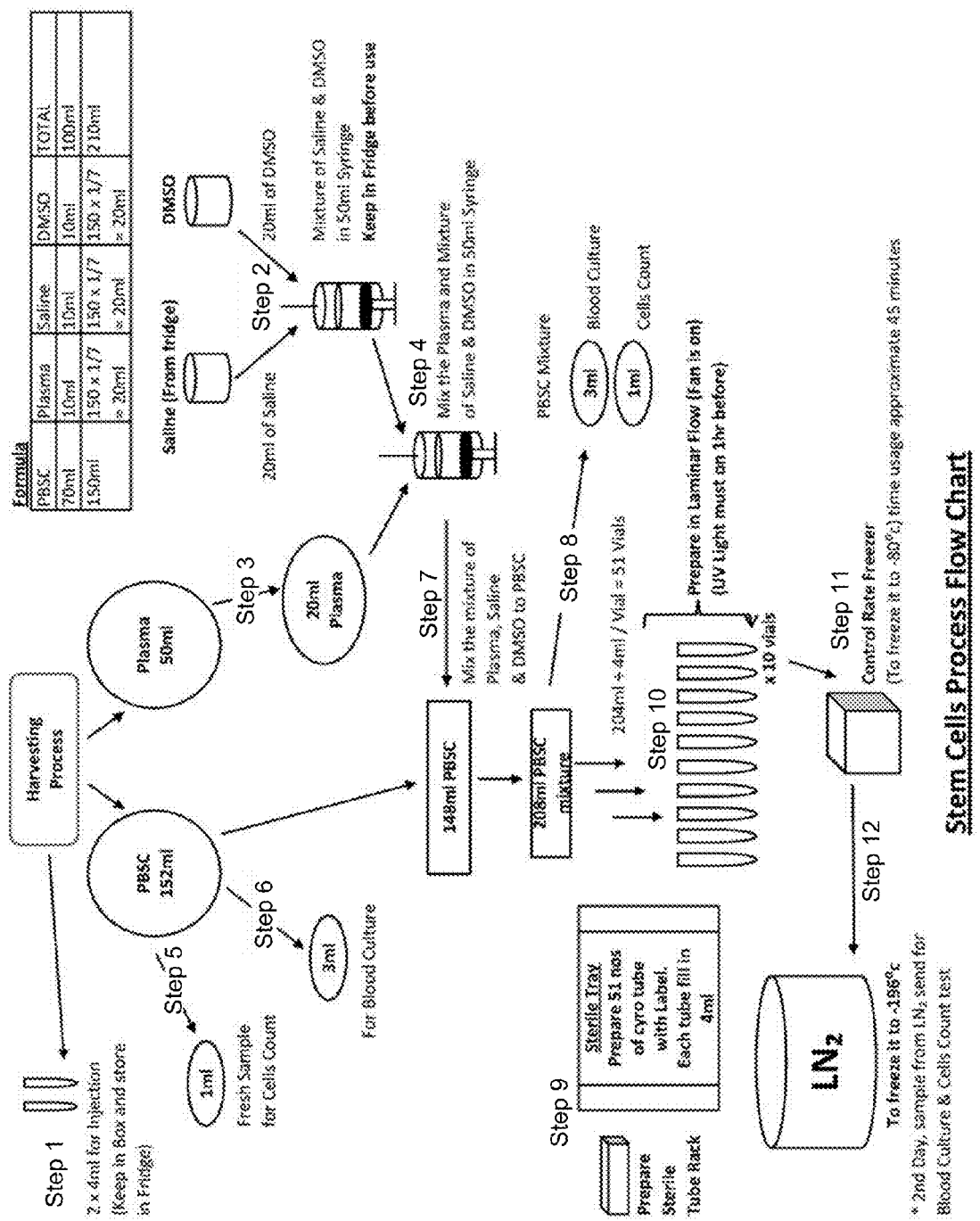
FIG. 32 shows one embodiment of a procedure involved in harvesting and storing stem cells.

One example of how the stem cells are harvested and stored is illustrated in FIG. 32 and the various steps 1-12 described below. Note that the specific amounts employed for the mixtures produced are exemplary only and it is to be realized that the amounts discussed below can vary as to scale and different amounts may be employed.

At step 1, an amount of harvested stem cells, for example, about $0.2\pm0.1\times10^{6\pm1}$ to about $8\pm1\times10^{6\pm2}$ of stem cells contained in two 4 ml vials, can be set aside and stored at a temperature of about 4° C. for immediate use. In some examples, the PBSCs are positive for CD34. In some examples, the stem cells can be PBSCs. In some examples, the PBSCs are positive for CD34. In some examples, the PBSCs can be autologous.

At steps 2 through 7, a storage mixture of saline (cooled from a refrigerator or an ice water bath at about 4° C.), plasma, dimethyl-disulphoxide (DMSO), and PBSCs is prepared. For example, in a 100 ml mixture, the following are used: 10 ml of saline; 10 ml of plasma; 10 ml of DMSO; and 70 ml of PBSCs. In another example, a 208 ml mixture includes 20 ml of saline, 20 ml of plasma, 20 ml of DMSO, and 148 ml of PBSCs (150 ml also may be used for a 210 ml total mixture). More particularly, step 2 shows the mixture of saline with DMSO that is kept in the refrigerator or an ice water bath before use at about 4° C. Step 3 shows obtaining 20 ml of the plasma from the patient's source. Step 4 shows the mixing of the plasma with the mixture of saline and DMSO. Steps 5 and 6 show that, prior to addition of the PBSCs to the mixture, about 1 ml of the PBSC source (e.g. 152 ml) is taken for a fresh sample cell count and 3 ml of the PBSC source is taken for blood culture, which leaves 148 ml of the PBSC source. Steps 5 and 6 are quality control steps during the process. Step 7 shows the mixing of the mixture of plasma, saline, and DMSO with the remaining PBSC source (e.g. 148 ml).

At step 8, another quality control step can be performed where 1 ml is taken for cell count and 3 ml is taken for blood culture.

At step 9, a sterile tube rack is prepared. In one embodiment, 20 to 80 cryo-tubes or vials are prepared with labelling (sterilised) and each tube/vial is filled with 4 ml of the mixture.

At step 10, the vials are prepared with laminar flow (e.g. Biosafety cabinet Class100 with or without fan on), where ultraviolet (UV) light has been on for about 10 minutes to 1 hour before use. That is, the UV light is turned off during the preparation or filling of the vials, and then the UV light is turned on to re-sterilize the compartment before using.

At step 11, the vials (e.g. about 20 to 80 vials at a time), are contained in a control rate freezer or any method providing a controlled rate during freezing from room temperature to about −80° C. for approximately 45 minutes.

At step 12, the vial samples are subject to freezing at −196° C. For example, 4 ml of the vial samples are frozen using liquid nitrogen ($LN_2$), where they can be thawed for later blood culturing and cell count testing. The frozen vials can be thawed, for example, after the second day of freezing. With further reference to FIG. 32, second day means the day after the vials were frozen in liquid nitrogen. For example, if the vials were frozen in liquid nitrogen on Monday, the second day would be Tuesday, at which time the vials can be taken out and thawed, so that the peripheral blood stem cell contents can be sent for blood culture.

To ensure that the vials are prepared and stored in sterile conditions, the following steps may be taken:
a. The cryovials were labeled with printed labels with patient's data.
b. The vials and caps are sterilized to ensure vial, caps and labels are entirely sterile.
c. The pre-labeled sterilized vials are placed in sterile rack for easy and quick aliquots.
d. The sterile caps are screwed on securely and capped prior to control rate freezer stage.

Yield and Viability

Table 1 below shows viability of the stem cell samples prepared in accordance with the process of FIG. 32.

TABLE 1

| Sample for Peripheral Blood Stem Cells (4 mls) | | | | | |
|---|---|---|---|---|---|
| Fresh | | Fresh with DMSO | | Frozen | |
| CD34 + ($10^6$ cells) | Viability % | CD34 + ($10^6$ cells) | Viability % | CD34 + ($10^6$ cells) | Viability % |
| 4.22 | 99.30 | 2.89 | 92.40 | 5.04 | 83.50 |
| 4.05 | 99.10 | 2.87 | 94.70 | 2.76 | 88.30 |
| 1.73 | 98.80 | 1.33 | 90.40 | 1.18 | 78.60 |
| 3.37 | 98.30 | 2.28 | 92.50 | 2.12 | 81.60 |
| 2.96 | 99.10 | 2.05 | 95.40 | 1.92 | 81.50 |
| 2.3 | 99.30 | 1.64 | 94.40 | 1.42 | 86.80 |
| 1.52 | 98.80 | 1.01 | 91.80 | 0.95 | 84.90 |
| 3.59 | 99.30 | 2.67 | 93.50 | 2.51 | 85.80 |
| 0.93 | 99.40 | 0.50 | 97.60 | 0.44 | 90.90 |
| 7.55 | 99.40 | 5.34 | 87.90 | 4.91 | 73.00 |
| 1.05 | 99.40 | 0.70 | 94.00 | 0.65 | 88.90 |
| 1.68 | 99.20 | 1.21 | 93.20 | 1.03 | 86.20 |
| 0.9 | 98.90 | 0.70 | 94.60 | 0.6 | 86.10 |
| 2.35 | 97.60 | 1.57 | 84.50 | 1.55 | 77.90 |
| 4.73 | 99.00 | 3.72 | 85.00 | 2.99 | 73.50 |
| 1.88 | 98.20 | 1.36 | 88.30 | 1.18 | 80.90 |
| 3.74 | 99.50 | 2.59 | 91.10 | 2.32 | 84.30 |

TABLE 1-continued

| Sample for Peripheral Blood Stem Cells (4 mls) | | | | | |
|---|---|---|---|---|---|
| Fresh | | Fresh with DMSO | | Frozen | |
| CD34 + ($10^6$ cells) | Viability % | CD34 + ($10^6$ cells) | Viability % | CD34 + ($10^6$ cells) | Viability % |
| 4.87 | 99.40 | 3.47 | 91.40 | 3.02 | 77.90 |
| 0.92 | 99.31 | 0.71 | 93.10 | 0.57 | 91.40 |
| 3.46 | 99.30 | 2.54 | 96.80 | 2.32 | 92.50 |
| Average 2.89 | 99.03 | 2.06 | 92.13 | 1.97 | 83.73 |

Table 1 provides a summary of cell count and yield for the following: fresh samples, fresh samples with DMSO, and post thaw of frozen samples, e.g. produced according to FIG. 32. From literature (Katayama et al, 1997, Bone Marrow Transplantation: 19: page 283-287, which is incorporated herein by reference), the cell viability of known frozen samples is reported to be approximately 80% and fresh samples with DMSO are between 69% to 80%. However, from the improved process disclosed herein it is shown that the samples are far superior with frozen samples, for example having a viability of over 83% on average and with fresh samples (w/ DMSO) having a viability of over 92% on average (lowest 84.5%). The results reported in Table 1 show that the process of FIG. 32 can provide good viability samples and a further improvement over known viability studies.

Referring back to FIG. 19, after step 473, the stem cells can be injected into the fibular osteotomy site 79 and/or the tibial osteotomy site 81 on a weekly basis (480). In some examples, the stem cells used can be, for example, the same type of cells used in step 473 as discussed above. In some examples, the amount of stem cells injected can be the same amount of stem cells as in step 473 as discussed above.

In some examples, the stem cells are injected once a week. In some examples, the stem cells are injected on a weekly basis, for example, once a week, for about one to about five weeks after step 473 is performed.

EXAMPLES

The effects on various human patients as a result of employing the concepts described herein are illustrated in the clinical example(s) below.

With reference to FIGS. 33-36, effects on human patients employing the methods described herein are illustrated.

Figure 33:
FIGS. 33-36 illustrate the effects on human patients employing the methods described herein.
Figure 34:
Figure 35:
Figure 36:

FIGS. 33-36 show an example of a patient who was subjected to the disclosed method. The patient is 50 years old. FIG. 33 shows an X-ray image of the right and left lower limbs of the patient. The right knee has a varus deformity. The left knee had a varus deformity but was treated by subjecting to a tibial osteotomy employing conventional methods. FIGS. 1A and 1B show the pre-operation plan to obtain the angle of correction for the size of the wedge opening of the right knee shown in FIG. 33. FIG. 34 shows an X-ray image of the right knee post-operation. The X-ray image shows an anteroposterio view of the right knee. FIG. 35 shows the same view of the right knee at 6 weeks post-operation. The X-ray shows bone callous formation at the osteotomy site. FIG. 36 shows the same view of the right knee at 5 months post-operation. The X-ray shows good bone callous formation.

With regard to the foregoing description, it is to be understood that changes may be made in detail, especially in matters of the construction materials employed and the shape, size and arrangement of the parts without departing from the scope of the present invention. It is intended that the specification and depicted embodiment to be considered exemplary only, with a true scope and spirit of the invention being indicated by the broad meaning of the claims.

What is claimed is:

1. An osteotomy guide device comprising:
a base including an elongated central portion that extends from a first end to a second end, thereby defining an axis, a first extending portion that extends from the first end of the central portion, a second extending portion that extends from the second end of the central portion, and a plurality of passageways, wherein the osteotomy guide device has a thickness and the passageways are formed through the thickness of the osteotomy guide device,
wherein the first extending portion is a latching portion,
wherein at least a portion of the device is configured to substantially follow at least a portion of an outline of a tibia or fibula as viewed in top view, the portion of the outline being below the tibial tuberosity,
wherein the passageways are configured to allow drilling to occur along the outline of the tibia or fibula below the tibial tuberosity as viewed in top view, and
wherein the latching portion is configured to latch onto the tibia or fibula below the tibial tuberosity so as to fix the device onto the tibia or fibula,
wherein the base has first and second sides,
wherein the first side faces the tibia or fibula when the device is fixed onto the tibia or fibula,
wherein the latching portion curves toward the first side and includes a tip,
wherein the first and second sides are coupled and converge at the tip, and
wherein the tip extends toward the second end and in a direction that is parallel to the axis.

2. The osteotomy guide device of claim 1, wherein the latching portion is in the shape of a hook.

3. The osteotomy guide device of claim 1, wherein the second extending portion is a flared portion.

4. The osteotomy guide device of claim 1, wherein the plurality of passageways include passageways that are adapted for positioning a direction of the drilling, and optionally wherein the passageways that are adapted for positioning the direction of the drilling are aligned along a median axis of the base.

5. The osteotomy guide device of claim 4, wherein each of the passageways that are adapted for positioning the direction of the drilling have an inlet and an outlet, wherein each of the passageways is configured to extend from the inlet to the outlet in a direction that is substantially parallel to or on the horizontal cross-sectional plane of a tibia or fibula so that drilling can occur in a direction that is substantially parallel to or on the horizontal cross-sectional plane of the tibia or fibula.

6. The osteotomy guide device of claim 1, wherein the plurality of passageways include one or more passageways that are adapted for inserting and/or positioning a wire, pin or screw and optionally wherein the one or more passageways that are adapted for inserting and/or positioning a wire, pin, or screw is provided along a first sagittal axis and/or a second sagittal axis.

7. The osteotomy guide device of claim 1, wherein the plurality of passageways include one or more passageways that is adapted for connecting with a handle wherein the one or more passageways that is adapted for connecting with the handle is provided along a first sagittal axis and/or a second sagittal axis.

8. The osteotomy guide device of claim 7, wherein the handle is connected to the osteotomy guide device.

9. A surgical kit for use in an osteotomy procedure comprising:
(i) the osteotomy guide device as claimed in claim 1; and
(ii) a bone spacer guide that is configured to maintain a wedge angle of a wedge opening that is formed as a result of an osteotomy using the osteotomy guide device.

10. The osteotomy guide device of claim 1, wherein each of the elongated central portion, the first extending portion and the second extending portion includes more than one passageway, and wherein the passageways extend along the same plane.

11. The osteotomy guide device of claim 1, wherein the passageways include intercrossing passageways within the base.

12. The osteotomy guide device of claim 11, wherein the intercrossing passageways are included in the central portion.

* * * * *